United States Patent
Shisa et al.

(10) Patent No.: US 9,732,338 B2
(45) Date of Patent: Aug. 15, 2017

(54) PROMOTER AND USE THEREOF

(71) Applicants: TOYOTA JIDOSHA KABUSHIKI KAISHA, Toyota-shi, Aichi (JP); YAMAGUCHI UNIVERSITY, Yamaguchi-shi, Yamaguchi (JP); JX NIPPON OIL & ENERGY CORPORATION, Chiyoda-ku, Tokyo (JP)

(72) Inventors: Noriko Shisa, Toyota (JP); Rinji Akada, Ube (JP); Hisashi Hoshida, Ube (JP); Kozue Mutaguchi, Chiyoda-ku (JP); Takeshi Uemura, Chiyoda-ku (JP); Kenro Tokuhiro, Nagakute (JP); Satoshi Katahira, Nagakute (JP)

(73) Assignees: TOYOTA JIDOSHA KABUSHIKI KAISHA, Aichi-ken (JP); YAMAGUCHI UNIVERSITY, Yamaguchi-shi (JP); JX NIPPON OIL & ENERGY CORPORATION, Tokyo (JP)

( * ) Notice: Subject to any disclaimer, the term of this patent is extended or adjusted under 35 U.S.C. 154(b) by 0 days.

(21) Appl. No.: 14/382,029

(22) PCT Filed: Mar. 4, 2013

(86) PCT No.: PCT/JP2013/001302
§ 371 (c)(1),
(2) Date: Aug. 29, 2014

(87) PCT Pub. No.: WO2013/128948
PCT Pub. Date: Sep. 6, 2013

(65) Prior Publication Data
US 2015/0031103 A1   Jan. 29, 2015

(30) Foreign Application Priority Data

Mar. 2, 2012 (JP) ................................. 2012-046539

(51) Int. Cl.
*C12N 15/113* (2010.01)
*C12N 15/81* (2006.01)
*C12P 7/10* (2006.01)

(52) U.S. Cl.
CPC .......... *C12N 15/113* (2013.01); *C12N 15/815* (2013.01); *C12P 7/10* (2013.01); *C12N 2320/50* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| 7,132,522 B1 | 11/2006 | Becher et al. |
| 2013/0210107 A1 | 8/2013 | Akada et al. |

FOREIGN PATENT DOCUMENTS

| WO | 94/13821 A1 | 6/1994 |
| WO | 01/20005 A1 | 3/2001 |
| WO | 2011/099263 A1 | 8/2011 |

OTHER PUBLICATIONS

Qian et al., Biotechnol. Lett. 33:571-575, 2011.*
Maria M. Ball, et al. "Construction of Efficient Centromeric, Multicopy and Expression Vectors for the Yeast *Kluyveromyces marxianus* Using Homologous Elements and the Promoter of a Purine-Cytosine-Like Permease", Journal of Molecular Microbiology and Biotechnology, Nov. 1, 1999, pp. 347-353, vol. 1, No. 2.
Ronald J. M. Bergkamp, et al., "Expression of an α-galactosidase gene under control of the homologous inulinase promoter in *Kluyveromyces marxianus*", Appl. Microbiol. Biotechnol., Jan. 1, 1993, pp. 309-317, vol. 40.
Olena P. Ishchuk, et al., "Development of a promoter assay system for the flavinogenic yeast *Candida famata* based on the *Kluyveromyces lactis* β-galactosidase LAC4 reporter gene", Enzyme and Microbial Technology, Jan. 15, 2008, pp. 208-215, vol. 42, No. 3.
Melanie M. Lane, et al., "*Kluyveromyces marxianus*: A yeast emerging from its sisters shadow", Fungal Biology Reviews, Feb. 1, 2010, pp. 17-26, vol. 24, No. 1-2.
Gustavo Graciano Fonseca, et al., "The yeast *Kluyveromyces marxianus* and its biotechnological potential", Appl. Microbiol Biotechnol, 2008, pp. 339-354, vol. 79.
Sanom Nonklang, et al., "High-Temperature Ethanol Fermentation and Transformation with Linear DNA in the Thermotolerant Yeast *Kluyveromyces marxianus* DMKU3-1042", Applied and Environmental Microbiology, 2008, pp. 7514-7521, vol. 74, No. 24.
Jesse Yonkovich, et al., "Accelerated Publication: Copper Ion-sensing Transcription Factor Mac1p Post-translationally Controls the Degradation of Its Target Gene Product Ctr1p", The Journal of Biological Chemistry, 2002, pp. 23981-23984, vol. 277, No. 27.
Marie-Therese Doolin, et al., "Overlapping and distinct roles of the duplicated yeast transcription factors Ace2p and Swi5p", Molecular Microbiology, 2001, pp. 422-432, vol. 20, No. 2.
Jiong Hong, et al., "Construction of thermotolerant yeast expressing thermostable cellulase genes", Journal of Biotechnology, 2007, pp. 114-123, vol. 130.

(Continued)

*Primary Examiner* — Nancy Treptow
(74) *Attorney, Agent, or Firm* — Sughrue Mion, PLLC

(57) ABSTRACT

The promoter of the present invention causes a desired gene to be highly expressed, especially in thermotolerant yeast. The promoter is located upstream of the PIR1 gene or the CTR1 gene on the *Kluyveromyces marxianus* chromosome and comprises a region controlling expression of the PIR1 gene or the CTR1 gene.

13 Claims, 7 Drawing Sheets

(56) References Cited

OTHER PUBLICATIONS

International Search Report for PCT/JP2013/001302 dated Jun. 21, 2013 [PCT/ISA/210].
Written Opinion for PCT/JP2013/001302 dated Jun. 21, 2013 [PCT/ISA/237].
Yamaguchi-Iwai et al., "Homeostatic Regulation of Copper Uptake in Yeast via Direct Binding of MAC1 Protein to Upstream Regulatory Sequences of FRE1 and CTR1", The Journal of Biological Chemistry, 1997, vol. 272, No. 28, p. 17711-17718.
Sumita et al., "Comparison of Cell Wall Localization among Pir Family Proteins and Functional Dissection of the Region Required for Cell Wall Binding and Bud Scar Recruitment of Pir1p", Eukaryot Cell, 2005, vol. 4, No. 11, pp. 1872-1881.

* cited by examiner

PROMOTER AND USE THEREOF

CROSS REFERENCE TO RELATED APPLICATIONS

This application is a National Stage of International Application No. PCT/JP2013/001302 filed Mar. 4, 2013, claiming priority based on Japanese Patent Application No. 2012-046539 filed Mar. 2, 2012, the contents of all of which are incorporated herein by reference in their entirety.

TECHNICAL FIELD

The present invention relates to a novel promoter that functions in thermotolerant yeast and the use thereof.

BACKGROUND ART

Yeast represented by *Saccharomyces cerevisiae* is widely used in the food industry by making use of its fermentation capacity and as a host for production of a variety of substances. In addition, yeast is a major study subject in the field of genetic engineering. As an example of yeast, yeast (also referred to as thermotolerant yeast) for which the optimal temperature range falls within a relatively high temperature range is known, as well as *Saccharomyces cerevisiae*.

A reaction system can be maintained within a relatively high temperature range using such thermotolerant yeast, making it possible to prevent contamination. In addition, it is necessary to culture yeast in a relatively high temperature range depending on the type of substance to be produced or reaction system. In such case, it is particularly preferable to use thermotolerant yeast.

As an aside, in general, when a given gene is expressed in yeast, a promoter that constantly allows high expression is used. Examples of known promoters that can be used in yeast include a TDH3 promoter, an ADH1 promoter, and a TEF1 promoter. In addition, Non-Patent Literature 1 discloses that a cellulase gene was expressed in thermotolerant yeast using a TDH3 promoter.

Although the above different promoters can constantly cause high expression of genes located downstream thereof in generally available yeast such as *Saccharomyces cerevisiae*, the expression levels of such downstream genes are insufficient when thermotolerant yeast is used as a host. That is, there is no conventionally known promoter that can cause high expression of a desired gene in thermotolerant yeast.

CITATION LIST

Non Patent Literature

NPL 1: Jiong Hong et al., Journal of Biotechnology 130 (2007) 114-123

SUMMARY OF INVENTION

Technical Problem

In view of the above circumstances, an object of the present invention is to provide a novel promoter capable of causing high expression of a desired gene, especially in thermotolerant yeast.

Solution to Problem

As a result of intensive studies in order to achieve the above object, the present inventors have succeeded in identifying a novel promoter capable of causing high expression of a gene of interest in thermotolerant yeast. This has led to the completion of the present invention. The present invention encompasses the following.

(1) A promoter, which is located upstream of the PIR1 gene on the *Kluyveromyces marxianus* chromosome and comprises a region controlling expression of the PIR1 gene.

(2) A promoter, which is located upstream of the CTR1 gene on the *Kluyveromyces marxianus* chromosome and comprises a region controlling expression of the CTR1 gene.

(3) The promoter according to (1), which comprises a nucleotide sequence consisting of at least 1000 nucleotides from the 3' end of the nucleotide sequence shown in SEQ ID NO: 1.

(4) The promoter according to (1), which comprises a nucleotide sequence consisting of at least 2000 nucleotides from the 3' end of the nucleotide sequence shown in SEQ ID NO: 1.

(5) The promoter according to (2), which comprises a nucleotide sequence consisting of at least 384 nucleotides from the 3' end of the nucleotide sequence shown in SEQ ID NO: 2.

(6) The promoter according to (2), which comprises a nucleotide sequence consisting of at least 429 nucleotides from the 3' end of the nucleotide sequence shown in SEQ ID NO: 2.

(7) A nucleic acid construct, which comprises the promoter according to any one of (1) to (6).

(8) An expression vector, which comprises the promoter according to any one of (1) to (6).

(9) The expression vector according to (8), which further comprises a gene located downstream of the promoter.

(10) A transformant, in which the promoter according to any one of (1) to (6) is inserted upstream of a desired gene.

(11) The transformant according to (10), wherein the desired gene is a foreign gene.

(12) The transformant according to (10), wherein a thermotolerant yeast cell is used as a host cell.

(13) The transformant according to (10), which is capable of causing saccharification of a cellulose-based biomass and ethanol fermentation.

(14) A method for producing a substance, comprising culturing the transformant according to any one of (10) to (13) and collecting a desired substance produced in a medium and/or the transformant after culture.

(15) The method for producing a substance according to (14), wherein the desired substance is ethanol synthesized via ethanol fermentation from a sugar obtained via saccharification of a cellulose-based biomass.

Advantageous Effects of Invention

The promoter of the present invention can cause high expression of a gene located downstream thereof even in thermotolerant yeast. In particular, the expression level of a desired gene can be increased for thermotolerant yeast using the promoter of the present invention.

Also, according to the method for producing a substance of the present invention, excellent productivity can be achieved for a desired substance because the expression level of a given gene can be improved using the above promoter. That is, according to the method for producing a substance of the present invention, productivity can be remarkably increased for proteins encoded by genes which

DESCRIPTION OF EMBODIMENTS

Figure 1:
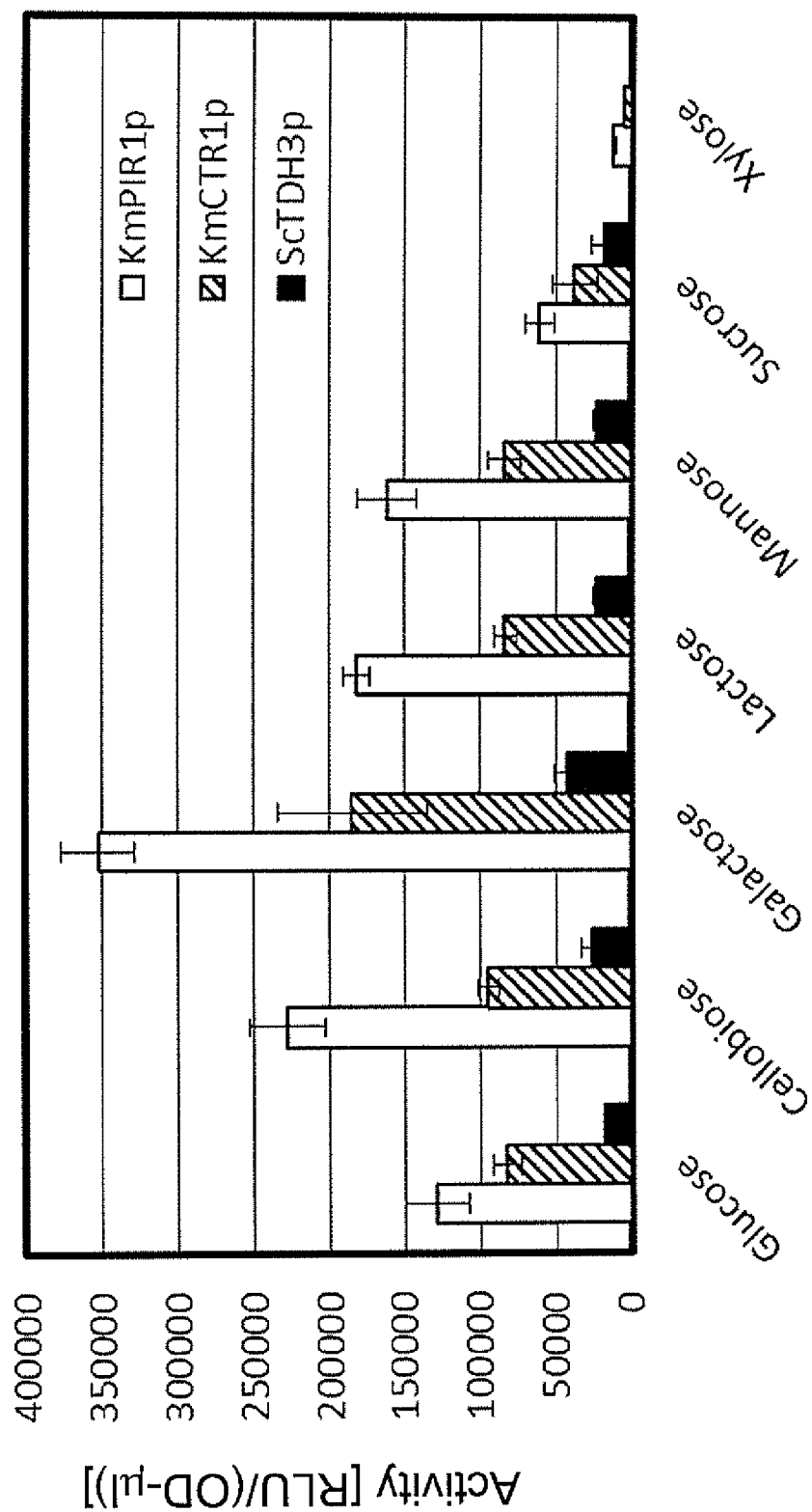
FIG. 1 is a characteristic chart showing reporter assay results for KmPIR1p, KmCTR1p, and ScTDH3p.

The present invention is described in more detail below with reference to the drawings and Examples.

The promoter of the present invention includes a PIR1 gene promoter and a CTR1 gene promoter in *Kluyveromyces marxianus*. The PIR1 gene promoter in *Kluyveromyces marxianus* corresponds to a region controlling the PIR1 gene expression on the chromosome of *Kluyveromyces marxianus*. Similarly, the CTR1 gene promoter in *Kluyveromyces marxianus* corresponds to a region controlling the CTR1 gene expression on the chromosome of *Kluyveromyces marxianus*.

The PIR1 gene is known as a gene controlled by transcription factor Swi5p in *Saccharomyces cerevisiae* (Overlapping and distinct roles of the duplicate yeast transcription factors Ace2p and Swi5p, Marie-Therese Doolin et al., Molecular Microbiology (2001) 40(2), 422-432). The PIR1 gene is also known to encode glycoprotein that constitutes cell walls. In addition, transcription factor Swi5 is known to control transcription of genes involved in cell cycles (Distinct Regions of the Swi5 and Ace2 Transcription Factors Are Required for Specific Gene Activation, Helen J. McBride et al., Vol. 274, No. 30, Issue of July 23, pp. 21029-21036, 1999).

In addition, the CTR1 gene is known to encode a transporter for copper ions in *Saccharomyces cerevisiae* (Copper Ion-sensing Transcription Factor Mac1p Post-translationally Controls the Degradation of Its Target Gene Product Ctr1p*, Jesse Yonkovich et al, THE JOURNAL OF BIOLOGICAL CHEMISTRY, Vol. 277, No. 27, Issue of July 5, pp. 23981-23984, 2002).

A promoter capable of controlling the expression of a gene located downstream thereof can serve as the promoter of the present invention. Such promoter may correspond to any region located upstream of the PIR1 gene or the CTR1 gene in *Kluyveromyces marxianus*. As an example of the nucleotide sequence of the promoter, the nucleotide sequence of a region comprising 2873 nucleotides upstream of the PIR1 gene in *Kluyveromyces marxianus* is shown in SEQ ID NO: 1. In addition, the nucleotide sequence shown in SEQ ID NO: 1 is read from the 5' end toward the 3' end. This means that the PIR1 gene is located downstream of (i.e., on the 3'-end side of) the nucleotide sequence shown in SEQ ID NO: 1 in *Kluyveromyces marxianus*. Similarly, the nucleotide sequence of a region comprising 840 nucleotides upstream of the CTR1 gene in *Kluyveromyces marxianus* is shown in SEQ ID NO: 2. Also, the nucleotide sequence shown in SEQ ID NO: 2 is read from the 5' end toward the 3' end. This means that the CTR1 gene is located downstream of (i.e., on the 3'-end side of) the nucleotide sequence shown in SEQ ID NO: 2 in *Kluyveromyces marxianus*.

More specifically, as an example of the promoter of the present invention, a promoter located upstream of the PIR1 gene in *Kluyveromyces marxianus* preferably comprises a region comprising 1000 nucleotides located upstream of the PIR1 gene (i.e., 1000 nucleotides on the 3'-end side of the nucleotide sequence shown in SEQ ID NO: 1). More preferably, it comprises a region comprising 2000 nucleotides located upstream of the PIR1 gene (i.e., 2000 nucleotides on the 3'-end side of the nucleotide sequence shown in SEQ ID NO: 1). A region comprising 1000 nucleotides located upstream of the PIR1 gene can be used as a promoter showing remarkably excellent expression promotion activity. In addition, a region comprising 2000 nucleotides located upstream of the PIR1 gene can be used as a promoter showing further excellent expression promotion activity.

Moreover, it is most preferable for a promoter located upstream of the PIR1 gene in *Kluyveromyces marxianus* to comprise a region comprising the nucleotide sequence shown in SEQ ID NO: 1. The region comprising the nucleotide sequence shown in SEQ ID NO: 1 can be used as a promoter showing the highest transactivation activity. Meanwhile, as an example of the promoter of the present invention, a promoter located upstream of the CTR1 gene in *Kluyveromyces marxianus* preferably comprises a region located further upstream of a region comprising 384 nucleotides of the CTR1 gene. Specifically, a promoter located upstream of the CTR1 gene preferably comprises a region between the 384th nucleotide from the 3' end of the nucleotide sequence shown in SEQ ID NO: 2 and a nucleotide on the 5'-end side of the 384th nucleotide. Particularly preferably, a promoter located upstream of the CTR1 gene comprises a region between the 384th nucleotide from the 3' end of the nucleotide sequence shown in SEQ ID NO: 2 and the 429th nucleotide from the same. These regions located upstream of the CTR1 gene can be used as promoters showing particularly high transactivation activity.

In addition, the promoter of the present invention may be defined using, as a reference sequence, the nucleotide sequence shown in SEQ ID NO: 1 or 2 as described above; however, a reference nucleotide sequence is not limited to the sequences shown in SEQ ID NOS: 1 and 2. For example, a reference nucleotide sequence may be a sequence of a polynucleotide having promoter activity and comprising 80% or more, preferably 90% or more, and more preferably 95% or more identity to the nucleotide sequence shown in SEQ ID NO: 1 or 2. Specifically, the promoter of the present invention may comprise a nucleotide sequence having 80% or more, preferably 90% or more, and more preferably 95% or more identity to the nucleotide sequence shown in SEQ ID NO: 1 or a region comprising 1000 nucleotides and preferably 200 nucleotides on the 3'-end side of the nucleotide sequence.

Further, the promoter of the present invention is defined to correspond to a nucleotide sequence having 80% or more, preferably 90% or more, and more preferably 95% or more identity to the nucleotide sequence shown in SEQ ID NO: 2 or a region between the 384th nucleotide from the 3' end and a nucleotide on the 5'-end side of the 384th nucleotide and preferably a region between the 384th nucleotide from the 3' end and the 429th nucleotide from the same.

Here, the value of identity is a value calculated as a percentage of nucleotides of a nucleotide sequence corresponding to nucleotides of the nucleotide sequence shown in SEQ ID NO: 1 or 2 upon alignment between the nucleotide sequence and the nucleotide sequence shown in SEQ ID NO: 1 or 2 using a sequence homology search program (sometimes referred to as homology search program).

Further, the promoter of the present invention is defined using, as a reference sequence, the nucleotide sequence shown in SEQ ID NO: 1 or 2; however a reference nucleotide sequence is not limited to the nucleotide sequences shown in SEQ ID NOS: 1 and 2. For example, the nucleotide sequence of a polynucleotide having promoter activity and comprising a nucleotide sequence derived from the nucleotide sequence shown in SEQ ID NO: 1 or 2 by substitution, deletion, addition, or insertion of one or a plurality of nucleotides may be a reference sequence. The expression "a plurality of nucleotides" used herein refers to, for example, 2 to 200 amino acids, preferably 2 to 100 amino acids, more preferably 2 to 50 amino acids, and most preferably 2 to 25 amino acids.

Furthermore, the promoter of the present invention may be defined using, as a reference sequence, the nucleotide sequence of a polynucleotide that has promoter activity and hybridizes under stringent conditions to a part or the whole of a polynucleotide comprising a nucleotide sequence complementally to, for example, the nucleotide sequence shown in SEQ ID NO: 1 or 2. Here, hybridization under stringent conditions refers to maintenance of coupling at 60 degrees C. during washing with 2×SSC. Hybridization can be carried out by a conventionally known method such as the method described in J. Sambrook et al. Molecular Cloning, A Laboratory Manual, 2nd Ed., Cold Spring Harbor Laboratory (1989).

In addition, it is possible to verify whether or not a polynucleotide having a certain nucleotide sequence has promoter activity via reporter assay using an appropriate host. The appropriate host used herein may be preferably thermotolerant yeast such as *Kluyveromyces marxianus*; however, yeast such as *Saccharomyces cerevisiae* also can be used. A reporter gene used for reporter assay is not limited. For example, a luciferase (LUC) gene or a beta-glucuronidase (GUS) gene can be used. Such assay using a reporter gene can be used in accordance with an appropriately modified version of a conventionally known protocol.

The promoter of the present invention described above functions to control expression of a gene located downstream thereof. Here, the term "downstream" refers to a transcription direction, i.e., the direction from the 5' end to the 3' end of a sense strand. A nucleic acid construct having an expression control region which shows excellent transcription activity even in thermotolerant yeast can be provided using the promoter of the present invention. In addition, the nucleic acid construct may comprise not only the promoter but also a cis-acting element that can improve transcription activity of the promoter. Such nucleic acid construct can be structured to have an restriction enzyme recognition sequence at both ends. In addition, it is also possible to incorporate the nucleic acid construct into, for example, a conventionally known expression vector. Specifically, when the promoter of the present invention is incorporated into an expression vector that can cause expression of a desired gene, an expression vector that can cause high expression of the gene in thermotolerant yeast can be provided.

Such expression vector can be produced by incorporating the above promoter into any conventionally known expression vector that is mainly used for transformation of a host cell. In addition, an expression vector comprising the above promoter may be introduced onto the chromosome of a host cell or conserved extrachromosomally. In addition, any expression vector such as a plasmid vector, a cosmid vector, or a phage vector can be used. It is possible for the expression vector used herein to comprise an enhancer, a selection marker, a replication initiation site, a multiple cloning site, and the like, in addition to the promoter.

When the expression vector is used for transformation of yeast, including thermotolerant yeast, a recombinant vector can be produced by incorporating a desired gene into the expression vector. When a host cell is transformed using this recombinant vector, high-level transcription of the gene takes place in the host cell. The host cell used herein is not particularly limited; however, it is preferably yeast, including thermotolerant yeast, and particularly preferably thermotolerant yeast.

The selection marker used herein is a gene introduced to serve as a marker for expression vector introduction. In general, a gene encoding a fluorescent protein or an enzyme that gives a color reaction, a gene that complements auxotrophy of a host, or a drug-resistant gene is used. In the present invention, an expression vector can be constructed using such a generally used selection marker gene.

Yeast that can be used as a host is not particularly limited; however, thermotolerant yeast is preferably used. Thermotolerant yeast refers to yeast that can proliferate in a higher temperature range than that for generally available yeast described below. The temperature that allows proliferation can be defined as the upper limit temperature at which a certain proliferation rate can be maintained. More specifically, thermotolerant yeast can be defined as yeast for which the temperature that allows proliferation is 40 degrees C. or more, preferably 42 degrees C. or more, and more preferably 45 degrees C. or more.

Examples of thermotolerant yeast include, but are not particularly limited to, *Kluyveromyces marxianus, Hansenula polymorpha, Candida glabrata, Issatchenkia orientalis*, and *Debaryomyces hansenii*.

In addition, yeast that can be used as a host is not limited to the above thermotolerant yeast, and a generally available yeast can be used. Examples of generally available yeast include *Candida Shehatae, Pichia stipitis, Pachysolen tannophilus, Saccharomyces cerevisiae*, and *Schizosaccharomyces pombe*. In particular, *Saccharomyces cerevisiae* is preferable.

Any method conventionally known as a yeast transformation method can be used as a method for introducing an expression vector comprising the promoter of the present invention into yeast. Specific examples of a method than can be used in the present invention include, but are not limited to, the electroporation method (Meth. Enzym., 194, p. 182 (1990)), the spheroplast method (Proc. Natl. Acad. Sci. USA, 75 p. 1929 (1978)), and the lithium acetate method (J. Bacteriology, 153, p. 163 (1983), Proc. Natl. Acad. Sci. USA, 75 p. 1929 (1978), Methods in yeast genetics, 2000 Edition: A Cold Spring Harbor Laboratory Course Manual).

As an aside, a gene located downstream of the promoter of the present invention is a gene intended to be expressed in host yeast such as thermotolerant yeast. The gene is not particularly limited and thus can be a gene that encodes any protein. For example, examples thereof include genes encoding a variety of enzymes involved in saccharification of a cellulose-based biomass and genes encoding a variety of enzymes involved in ethanol fermentation using a sugar from the biomass. Specific examples of the gene include an alkaline protease gene, an alpha-amylase gene, an ascorbate oxidase gene, an aspartic protease gene, a cellobiohydrolase gene, a cellulase gene, a cutinase gene, an endoglucanase gene, a glucoamylase, a beta-glucosidase gene, a glyoxal oxidase gene, a laccase gene, a lignin oxidase gene, a lignin peroxidase gene, a lipase gene, a manganese peroxidase gene, a 1,2-alpha-mannosidase gene, a nuclease gene, a pectin lyase gene, a pectin methylesterase gene, an acid phosphatase gene, a polygalacturonase gene, a xylanase gene, and a beta-xylosidase gene.

More specifically, examples of genes encoding a variety of enzymes involved in ethanol fermentation of a sugar from a biomass include genes encoding enzymes involved in xylose metabolism (i.e., xylose-metabolism-related genes). Xylose-metabolism-related genes include a xylose reductase gene encoding xylose reductase that converts xylose into xylitol, a xylitol dehydrogenase gene encoding xylitol dehydrogenase that converts xylitol into xylulose, a xylulokinase gene encoding xylulokinase that phosphorylates xylulose so as to produce xylulose-5-phosphate, and a xylose isomerase gene encoding xylose isomerase that converts xylose into xylulose. In addition, xylulose-5-phosphate produced by xylulokinase enters a pentose phosphate pathway so as to be metabolized.

Xylose-metabolism-related genes introduced into the yeast genome are not particularly limited. However, examples thereof include: a xylose reductase gene and a xylitol dehydrogenase gene from *Pichia stipitis*; and a xylulokinase gene from *Saccharomyces cerevisiae* (see Eliasson A. et al., Appl. Environ. Microbiol, 66:3381-3386 and Toivari M N et al., Metab. Eng. 3:236-249). Other examples of xylose reductase genes that can be used include a *Candida tropicalis*-derived or *Candida prapsilosis*-derived xylose reductase gene. Examples of a xylitol dehydrogenase gene that can be used include a *Candida tropicalis*-derived or *Candida prapsilosis*-derived xylitol dehydrogenase gene. Examples of xylulokinase genes that can be used include a *Pichia stipitis*-derived xylulokinase gene. Also, a *Streptomyces murinus* cluster-derived xylose isomerase gene and the like can be used.

Genes encoding a variety of enzymes involved in ethanol fermentation of a sugar from a biomass may be genes encoding a variety of enzymes involved in ethanol fermentation of sugars such as cellobiose, galactose, lactose, mannose, and sucrose, in addition to the above xylose-metabolism-related genes.

Meanwhile, a variety of desired substances can be produced using the promoter of the present invention and yeast such as thermotolerant yeast. Here, a substance to be produced is any of a protein encoded by a gene transcribed at a high level by the above promoter and a substance to be produced using the protein. An example of a substance to be produced using the protein is a metabolism product for which the protein is involved as an enzyme in the metabolism pathway.

Here, a protein to be produced is not limited, and thus it may be a protein with any molecular weight from any organism species having any isoelectric point and comprising any amino acid sequence. In particular, examples of a protein to be produced include the following proteins encoded by genes from higher organisms: lysozyme, chymosin, lectin, interleukin, lactoferrin, an antibody drug such as an antiFas antibody, mite allergen, pollen allergen, cellulose-degrading enzyme for degradation of woody biomass, and cytokine.

In addition, when the protein is cellulase, an example of a substance to be produced using the protein is a sugar obtained via a saccharification reaction using, as a substrate, cellulose contained in a medium. Further, when genes encoding a variety of enzymes involved in ethanol fermentation are highly expressed in thermotolerant yeast using the promoter of the present invention, ethanol is a substance to be produced.

If a substance to be produced is produced via extracellular secretion, the substance can be collected by a standard method without disrupting cells. In addition, if a substance to be produced is intracellularly produced, cells are disrupted, and then the substance can be collected according to a standard method. If a substance to be produced is a protein, measurement can be carried out by directly analyzing a medium supernatant sample or a supernatant sample obtained after cell disruption via sodium dodecyl sulfate polyacrylamide gel electrophoresis (SDS-PAGE) known in the art. In this case, the desired protein produced during cell culture is secreted in a medium, and then the protein is purified or isolated by, for example, removing unnecessary components from the cell medium. In order to purify the desired protein, for example, techniques such as affinity chromatography, ion-exchange chromatography, hydrophobic interaction chromatography, ethanol precipitation, reversed-phase HPLC, cation-exchange resin (i.e., silica or DEAE) chromatography, chromatofocusing, SDS-PAGE, ammonium sulfate precipitation, and gel filtration can be used alone or in combination.

If a substance to be produced is ethanol, ethanol is collected from a medium in which yeast has been cultured. A method for collecting ethanol is not particularly limited, and thus any conventionally known method can be used. For example, after the completion of ethanol fermentation described above, a liquid layer containing ethanol is separated from a solid phase containing recombinant yeast and a solid component via solid-liquid separation. Then, ethanol contained in the liquid phase is isolated/purified by distillation. Thus, high-purity ethanol can be collected. The degree of ethanol purification can be adequately adjusted in accordance with the purpose of the use of ethanol.

In particular, the promoter of the present invention is preferably used for ethanol production via so-called "simultaneous saccharification and fermentation" using a cellulose-based biomass. In such case, the promoter of the present invention is ligated to a gene encoding an enzyme involved in a reaction used for ethanol fermentation of sugar components other than glucose (e.g., xylose) contained in a cellulose-based biomass, and then the promoter ligated to the gene is introduced into thermotolerant yeast (recombinant thermotolerant yeast). Examples of sugar components other than glucose include xylose, cellobiose, galactose, lactose, mannose, and sucrose.

Simultaneous saccharification and fermentation refers to a reaction system in which a saccharification reaction for decreasing the molecular weight of a polysaccharide such as cellulose or hemicellulose contained in a medium and ethanol fermentation for synthesizing ethanol from a sugar (mainly monosaccharide) produced in the saccharification reaction simultaneously progress. A saccharification reaction is, for example, a reaction in which endoglucanase that randomly acts on cellulose chains to produce cellooligosaccharide, cellobiohydrolases I and II that act on the ends of cellulose chains to produce cellobiose, and beta-glucosidase that acts on produced oligosaccharide to produce glucose, i.e., a monosaccharide are involved. These enzymes are collectively referred to as cellulase in some cases. Commercially available cellulase formulations can be used in a saccharification reaction for simultaneous saccharification and fermentation. In addition, hemicellulase that hydrolyzes hemicellulose to obtain a low-molecular-weight substance can be used in a saccharification reaction for simultaneous saccharification and fermentation.

Thermotolerant yeast into which the promoter of the present invention and the above gene have been introduced can be subjected to simultaneous saccharification and fermentation at an optimal growth temperature within a high temperature range. Specifically, the above gene can be expressed within a high temperature range including an optimal growth temperature, and thus ethanol productivity upon ethanol fermentation can be improved. Further, the high temperature range including an optimal growth temperature for thermotolerant yeast corresponds to a high temperature range in which high reaction rates can be achieved for the above cellulase, hemicellulose, and the like. Therefore, saccharification efficiency can be improved by carrying out simultaneous saccharification and fermentation within the high temperature range including an optimal growth temperature for thermotolerant yeast. In other words, the amount of enzyme required to achieve desired saccharification efficiency can be reduced. As described above, as a result of simultaneous saccharification and fermentation with the use of recombinant thermotolerant yeast into which the promoter of the present invention and the above gene have been introduced, cost reduction and the improvement of ethanol yield can be achieved for ethanol production with the use of a cellulose-based biomass.

In addition, temperature conditions for simultaneous saccharification and fermentation preferably comprise, but are not limited to, an optimal growth temperature for the above recombinant thermotolerant yeast. For example, temperature conditions for simultaneous saccharification and fermentation can be 20 to 50 degrees C., preferably 30 to 50 degrees C., and more preferably 35 to 45 degrees C. In addition, the pH of a culture solution is preferably adjusted to 4 to 6. Further, agitation or stirring may be performed during culture.

EXAMPLES

The present invention is hereafter described in greater detail with reference to the following examples, although the technical scope of the present invention is not limited thereto.

Example 1

In this Example, a PIR1 gene promoter and a CTR1 gene promoter in *Kluyveromyces marxianus*, which is thermotolerant yeast, were isolated and evaluated in terms of promoter activity by a reporter assay method.

First, chromosomal DNA of *Kluyveromyces marxianus* was prepared according to a standard method. PCR was performed using the obtained chromosomal DNA as a template, KmCTR1-1085 (TAGGATCAGGAGACAATC-GATATTA (SEQ ID NO: 3)) and CLuc+30c-KmCTR1-1c2 (caaagcgacagccaagatcaaggtcttcatCTTGATTGTTCAATT-GTCAATTGTC (SEQ ID NO: 4)) as primers, and KOD plus DNA polymerase (Toyobo). After the completion of PCR, the reaction solution was subjected to electrophoresis to obtain a DNA band of interest.

In addition, chromosomal DNA of the *Saccharomyces cerevisiae* RAK4296 strain (MATa his3 200 leu2 0 met15 0 trp1-delta-63 ura3 0::ScGAL10p-yCLuc-15C-LEU2) was prepared according to a standard method. PCR was performed using the obtained chromosomal DNA as a template, yCLuc+1 (ATGAAGACCTTGATCTTGGC (SEQ ID NO: 5)) and URA3-280c (CAGTCTGTGAAACATCTTTCTAC (SEQ ID NO: 6)) as primers, and KOD plus DNA polymerase. After the completion of PCR, the reaction solution was subjected to electrophoresis to obtain a DNA band of interest.

Fusion PCR was performed using a mixture of the two DNA fragments obtained above and primers KmCTR1p-1086 and URA3-280c. As a result, DNA comprising the two fused DNA fragments was obtained. The thus obtained DNA fragment has a structure comprising a luciferase gene fused downstream of the CTR1 gene promoter of *Kluyveromyces marxianus*. In addition, this DNA fragment contains, as a selection marker gene, the URA3 gene.

Similarly, PCR was performed using chromosomal DNA of *K. marxianus* as a template, KmPIR1-2867 (GGAAAGAGTCGATGTGATTCGATGC (SEQ ID NO: 7)) and 10tg-KmPIR1-1c (tgtgtgtgtgtgtgtgtgTG-TATAAATCGGGGTATGTG (SEQ ID NO: 8)) as primers, and KOD plus DNA polymerase. After the completion of PCR, the reaction solution was subjected to electrophoresis to obtain a DNA band of interest. Further, PCR was performed using chromosomal DNA of the *S. cerevisiae* RAK4296 strain as a template, 10CA-yCLuc+1 (cacacaca-cacacacacacaATGAAGACCTTGATCTTGGC (SEQ ID NO: 9)) and URA3-280c as primers, and KOD plus DNA polymerase. After the completion of PCR, the reaction solution was subjected to electrophoresis to obtain a DNA band of interest.

Fusion PCR was performed using a mixture of the two DNA fragments obtained above and primers KmPIR1-2867 and URA3-280c. As a result, DNA comprising the two fused DNA fragments was obtained. The thus obtained DNA fragment has a structure comprising a luciferase gene fused downstream of the PIR1 gene promoter of *Kluyveromyces marxianus*. In addition, this DNA fragment contains, as a selection marker gene, the URA3 gene.

Meanwhile, the TDH3 gene promoter in *S. cerevisiae* was evaluated in terms of promoter activity by reporter assay in a similar manner. ScTDH3-promoter-added yCLuc (ATTO Corporation) was subjected to PCR using chromosomal DNA of the *S. cerevisiae* RAK4920 strain (MATa his3 200 leu2 0 met15 0 trp1-delta-63 ura3 0::ScTDH3p-yCLuc-15C-LEU2) as a template and URA3-290 (GA-GAAGGGCAACGGTTCATCATCTC (SEQ ID NO: 10)) and 15G-yCLuc+1662c (ggggggggggggggggCTACTTG-CACTCATCTGGGA (SEQ ID NO: 11)) as primers.

After the completion of PCR, the reaction solution was subjected to electrophoresis to obtain a DNA band of interest. In addition, PCR was performed using chromosomal DNA of the *S. cerevisiae* BY4704 strain (MATa ade2-::hisG his3-200 leu2-0 lys2-0 met15-0 trp1-63) as a template and 15C-URA3-223 (ccccccccccccccccaagcttttcaat-tcatcttttttttttttg (SEQ ID NO: 12)) and URA3-280c as primers. After the completion of PCR, the reaction solution was subjected to electrophoresis to obtain a DNA band of interest.

Fusion PCR was performed using a mixture of the two DNA fragments obtained above and primers URA3-290 and URA3-280c. As a result, DNA comprising the two fused DNA fragments was obtained. The thus obtained DNA fragment has a structure comprising a luciferase gene fused downstream of the TDH3 gene promoter of *Kluyveromyces marxianus*. In addition, this DNA fragment contains, as a selection marker gene, the URA3 gene.

Next, the RAK4174 strain (*K. marxianus* leu2⁻ ura3⁻) was transformed with each of the three different DNA fragments obtained above. Transformation was carried out in the following manner. First, shake culture was carried out using a YPD medium at 28 degrees C. and 150 rpm for one day. The obtained culture solution (1.5 ml) was centrifuged at 12,000 rpm for 1 minute. The supernatant was discarded, and TF buffer (40% polyethylene glycol 3350, 0.2 M lithium acetate, and 0.1 M dithiothreitol) (200 microliters) was added, followed by stirring mixing for 15 seconds. Then, the mixture was centrifuged at 12,000 rpm for 1 minute and the supernatant was discarded. The resultant was suspended in TF buffer (50 microliters). DNA (3 microliters) was added, followed by heat shock treatment at 47 degrees C. for 15 minutes. The obtained cells were seeded on an uracil-deficient solid medium and subjected to static culture at 28 degrees C. for 3 days. Colonies grown on the solid medium were randomly selected and subjected to activity measurement in the manner described below.

The strain obtained by transforming the RAK4174 strain with a DNA fragment having a structure comprising a luciferase gene fused downstream of the PIR1 gene promoter was designated the "*K. marxianus* RAK5689 strain." In addition, the strain obtained by transforming the RAK4174 strain with a DNA fragment having a structure comprising a luciferase gene fused downstream of the CTR1 gene promoter was designated the "*K. marxianus* RAK5686 strain."

Each culture solution comprising a YP medium and a different sugar at a concentration of 2% was cultured at 28 degrees C. for 48 hours and sampled, followed by activity measurement. Cluc measurement kits (ATTO Corporation) and a luminometer GLOMAX 20/20 LUMINOMETER (Promega) were used for measurement. Sugars used herein were glucose, cellobiose, galactose, lactose, mannose, sucrose, and xylose. FIG. 1 shows the measurement results. In FIG. 1, KmPIR1p represents promoter activity of the PIR1 promoter of *K. marxianus*, KmCTR1p represents promoter activity of the CTR1 promoter of *K. marxianus*, and ScTDH3p represents promoter activity of the *S. cerevisiae* TDH3 promoter.

As shown in FIG. 1, the PIR1 promoter of *K. marxianus* and the CTR1 promoter of *K. marxianus* were found to have excellent promoter activity in *K. marxianus* over the TDH3 promoter of *S. cerevisiae* generally used as a high expression promoter. A comparison between the PIR1 promoter of *K. marxianus* and the CTR1 promoter of *K. marxianus* revealed that the PIR1 promoter of *K. marxianus* shows superior promoter activity with the use of any sugar selected from among the above compared with the CTR1 promoter.

As an aside, in this Example, many *K. marxianus*-derived promoters were evaluated in terms of promoter activity. Specifically, PCR was performed using chromosomal DNA of *Kluyveromyces marxianus* prepared in the manner described above and a set of primers listed in table 1 below, followed by electrophoresis. Thus, a DNA band of interest was obtained. In addition, PCR was performed using chromosomal DNA of the *Saccharomyces cerevisiae* RAK4296 strain (MATa his3 200 leu2 0 met15 0 trp1-delta-63 ura3 0::ScGAL10p-yCLuc-15C-LEU2), yCLuc+1 and URA3-280c as primers, KOD plus DNA polymerase, followed by electrophoresis. Thus, a DNA band of interest was obtained. Fusion PCR was performed using a mixture of the thus obtained two DNA fragments so as to obtain DNA comprising the two fused DNA fragments. The obtained DNA fragment was introduced into the *K. marxianus* RAK4174 strain in the manner described above. Then, the promoter activity in a YPD medium was determined.

TABLE 1

| Gene name | Primer name | Nucleotide sequence | |
|---|---|---|---|
| MQFS378 | KmMQFS378-3560 | GGCGGATAAAATGGTACTATTACGT | SEQ ID No: 13 |
| | yCLuc + 30cMQFS378-1c | caaagcgacagccaagatcaaggtcttcatTTTTGATTTGTGTTTAAGCGAGTGA | SEQ ID No: 14 |
| MIFP960 | KmMIFP960-1745 | CTATTGCTTCGCTTCCCTGCATCAG | SEQ ID No: 15 |
| | yCLuc + 30cMIFP960-1c | caaagcgacagccaagatcaaggtcttcatGTCTGCTAAAAGTTCAAAATTAATT | SEQ ID No: 16 |
| HSP26 | KmHSP26-1110 | TTGGGCTAGAGCAAAAAACCCCAAC | SEQ ID No: 17 |
| | yCLuc + 30cKmHSP26-1c | caaagcgacagccaagatcaaggtcttcatCTCGTAATCGCTTTTGTTCTTAGTT | SEQ ID No: 18 |
| TEF1 | KmTEF1-1679 | GTGTTGTAACAAGCTGCCATATAGA | SEQ ID No: 19 |
| | yCLuc + 30cKmTEF1p-1c | caaagcgacagccaagatcaaggtcttcatCTTTAATGTTACTTCTCTTGGAGTT | SEQ ID No: 20 |
| PCK1 | KmPCK1-1599 | ATATCGTCTTATTCCATTAATAACC | SEQ ID No: 21 |
| | yCLuc + 30cKmPCK1-1c | caaagcgacagccaagatcaaggtcttcatGGTGACTTATTATTATTAGAAACAA | SEQ ID No: 22 |
| MVSI990 | MVSI990-2345 | TTCTAGTTGTTGGTTGTTGTTTTTG | SEQ ID No: 23 |
| | yCLuc + 30cMVSI990-1c | caaagcgacagccaagatcaaggtcttcatCTTTTAAAATTATCTGAGTTGAGTT | SEQ ID No: 24 |
| MAIP1047 | MAIP1047-1990 | GTCACGTGTGTATCCGGCGGGTAAA | SEQ ID No: 25 |
| | yCLuc + 30cMAIP1047-1c | caaagcgacagccaagatcaaggtcttcatTGTGTTGTGTATGATTTTGTTTTTA | SEQ ID No: 26 |

TABLE 1-continued

| Gene name | Primer name | Nucleotide sequence | |
|---|---|---|---|
| MLRL1128 | MLRL-720 | GAGTGCGGAGTCAGATACAA | SEQ ID No: 27 |
| | yCLuc + 30cMLRL1128-1 | caaagcgacagccaagatcaaggtcttcatTGTTGCGTGATATTTTCTGTGCCTG | SEQ ID No: 28 |

In table 1, the names of the genes corresponding to the promoters used in this Example are written in the "Gene name" column for notation of gene name, a combination of four alphabetical letters and at least one numeric character is used in the "Gene name" column as described in the Reference Experiments below.

Figure 2:
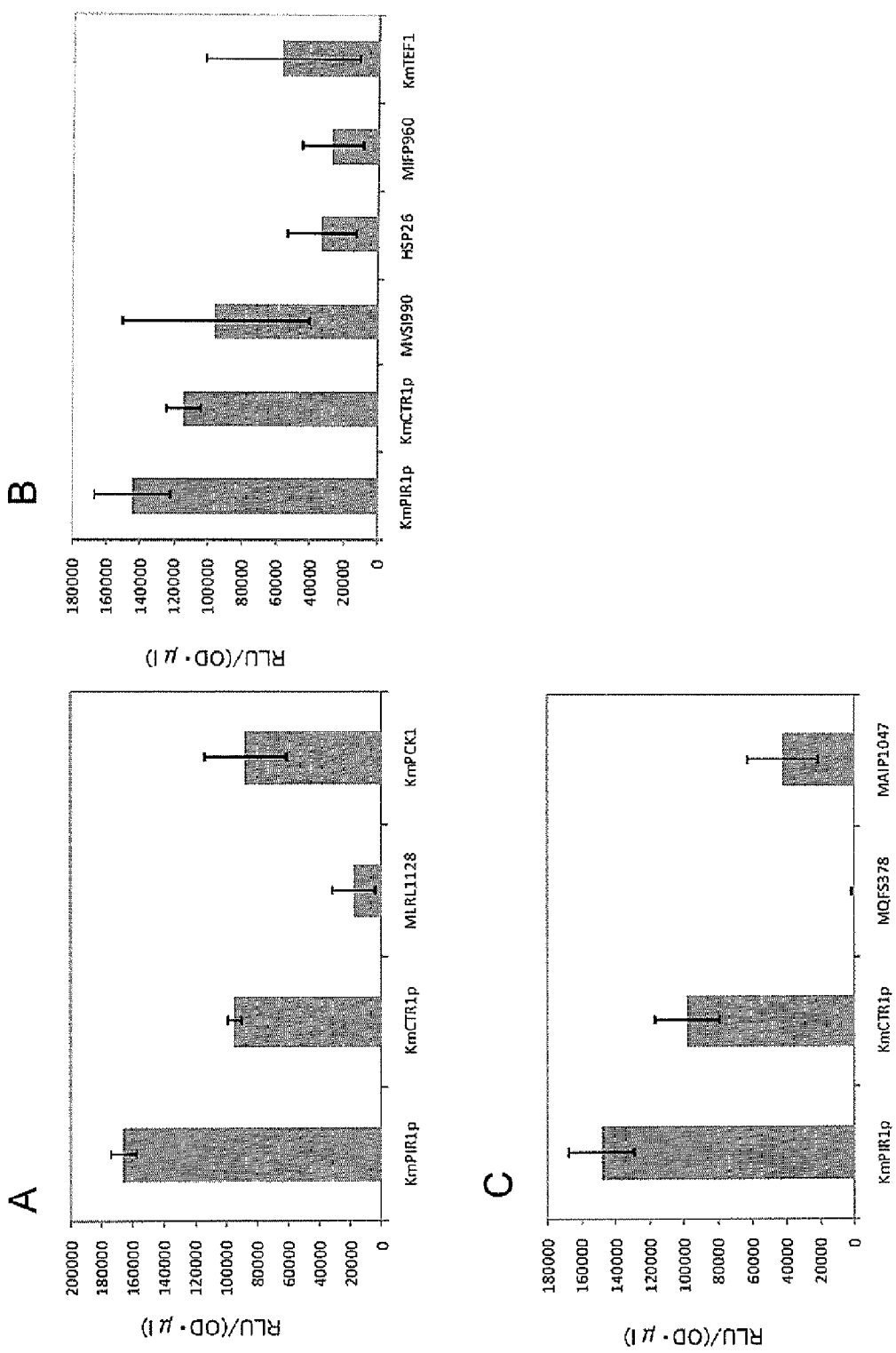
FIG. 2 is a characteristic chart showing reporter assay results for KmPIR1p, KmCTR1p, and other promoters.

FIGS. 2A-C shows promoter activity measurement results for the promoters, with the promoter activity measurements results for the PIR1 promoter of *K. marxianus* and the CTR1 promoter of *K. marxianus*. As shown in FIGS. 2A-C, the PIR1 promoter of *K. marxianus* and the CTR1 promoter of *K. Marxianus* were found to have excellent promoter activity over the many other gene promoters. In addition, the TEF1 gene, the HSP26 gene, and the PCK1 gene evaluated in this Example were genes which were relatively highly expressed upon xylose assimilation or glucose assimilation by *K. marxianus* as described in the Reference Examples below. Accordingly, the promoters of the TEF1 gene, the HSP26 gene, and the PCK1 gene were predicted as promoters capable of inducing high expression in *K. marxianus*. As described in this Example, however, the PIR1 promoter of *K. marxianus* and the CTR1 promoter of *K. marxianus* were found to shows superior promoter activity compared with these promoters expected as high expression promoters.

Example 2

In this Example, the PIR1 promoter of *K. marxianus* and the CTR1 promoter of *K. marxianus* evaluated in Example 1 were examined in terms of the functional region.

Specifically, PCR was performed using chromosomal DNA of the RAK5689 strain prepared in Example 1 as a template, the URA3-280c primer, and each of the primers listed in table 2. That is, as a result of PCR, DNA fragments each comprising a luciferase gene fused with a different one of DNA fragments having different lengths obtained by cleaving the PIR1 promoters evaluated in Example 1 on the 5'-end side were synthesized. Each PCR-amplified fragment was introduced into the *K. marxianus* RAK4174 strain, followed by luciferase activity measurement in the manner described in Example 1.

TABLE 2

| KmPIR1-2867 | GGAAAGAGTCGATGTGATTCGATGC | SEQ ID NO: 7 |
|---|---|---|
| KmPIR1p-2000 | GCAAAGCCCGATCCGGTTCTAA | SEQ ID NO: 29 |
| KmPIR1p-1023 | CAATCCCCTCGTTTCTCGCTTA | SEQ ID NO: 30 |
| KmPIR1p-500 | GGAATCAGGAACCGAAGGCGTT | SEQ ID NO: 31 |
| KmPIR1p-254 | CGGTTTATCCACACCATACCAT | SEQ ID NO: 32 |

Figure 3:
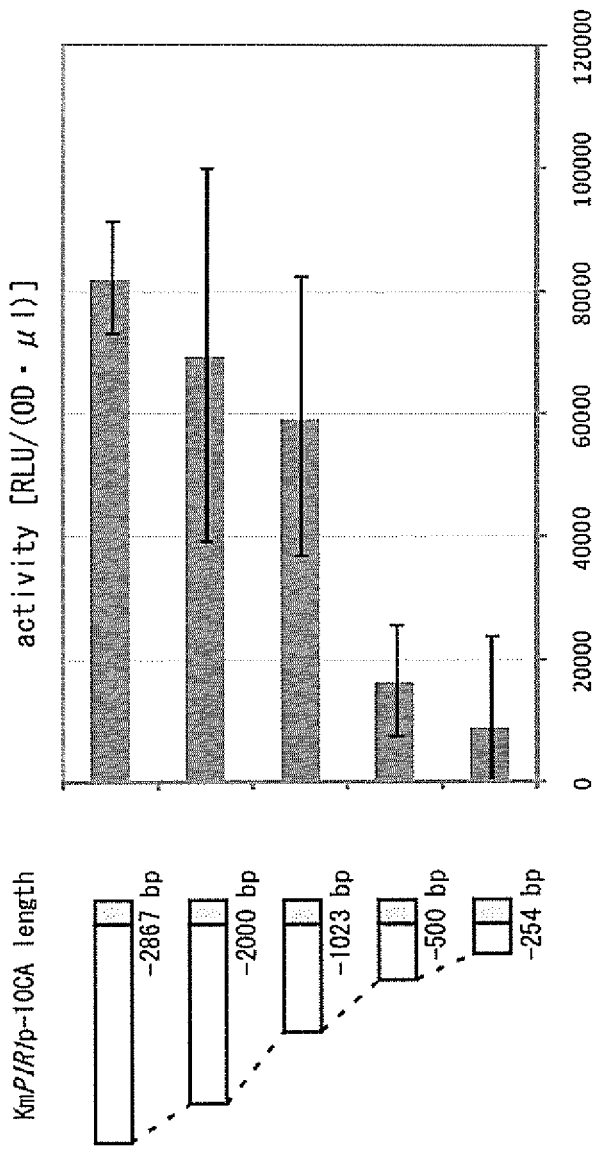
FIG. 3 is a characteristic chart showing reporter assay results for the functional region of KmPIR1p.

FIG. 3 shows the lengths of the evaluated DNA fragments and luciferase activity measurement results. As shown in FIG. 3, it was revealed that a DNA fragment with a length of about 1000 nucleotides exceeding 500 nucleotides upstream of the PIR1 gene shows significant promoter activity. It was also revealed that a DNA fragment with a length of about 2000 nucleotides upstream of the PIR1 gene shows further excellent promoter activity. In particular, the DNA fragments evaluated in Example 1 were revealed to show the most excellent promoter activity.

Also, the functional region of the CTR1 promoter was examined as follows. Specifically, PCR was performed using chromosomal DNA of the RAK5686 strain prepared in Example 1 as a template, the URA3-280c primer, and each of the primers listed in table 3. That is, as a result of PCR, DNA fragments each comprising a luciferase gene fused with a different one of DNA fragments having different lengths obtained by cleaving the CTR1 promoters evaluated in Example 1 on the 5'-end side were synthesized. Each PCR-amplified fragment was introduced into the *K. marxianus* RAK4174 strain, followed by luciferase activity measurement in the manner described in Example 1.

TABLE 3

| KmCTR1-1085 | TAGGATCAGGAGACAATCGATATTA | SEQ ID NO: 3 |
|---|---|---|
| KmCTR1p-474 | GCTAGAAAACCGTTGTAACACTG | SEQ ID NO: 33 |
| KmCTR1p-429 | CTCTCACATTGTTACTTTGAGC | SEQ ID NO: 34 |
| KmCTR1p-384 | GGTGCTGAAAAGTGCCTGTA | SEQ ID NO: 35 |
| KmCTR1p-314 | CTCTCTTTCTCTCTTCGTTTTTCTT | SEQ ID NO: 36 |

Figure 4:
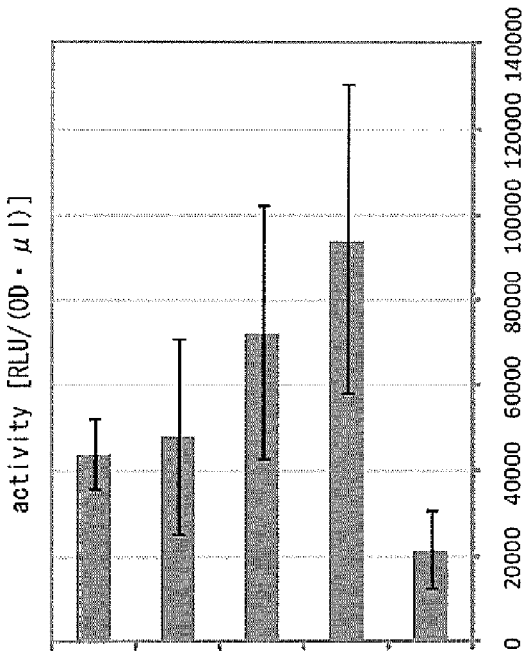
FIG. 4 is a characteristic chart showing reporter assay evaluation results for the functional region of KmCTR1p.
Figure 4:
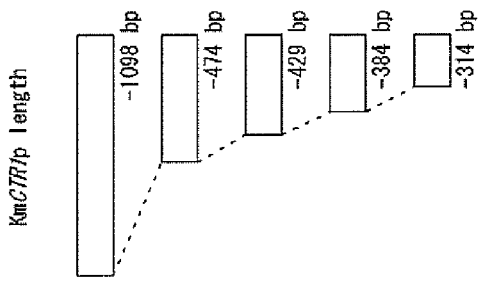

FIG. 4 shows lengths and luciferase activity measurement results for the evaluated DNA fragments. As shown in FIG. 4, it was revealed that a DNA fragment having a length of about 384 nucleotides exceeding 314 nucleotides upstream of the CTR1 gene shows the most significant promoter activity. In addition, a DNA fragment with a length exceeding 429 nucleotides upstream of the CTR1 gene was found to show excellent promoter activity, although which is lower than that for a DNA fragment with a length of about 384 nucleotides.

Example 3

In this Example, the PIR1 promoter of *K. marxianus* and the CTR1 promoter of *K. marxianus* evaluated in Example 1 were used as promoters for introducing a foreign gene into thermotolerant yeast so as to evaluate their promoter activity.

[Production of xyl1/xyl2 Double Deletion Mutant Transfected with the XI Gene]

A vector for deleting the xyl2 gene of the RAK6163 xyl1 deletion strain (xyl1::ScURA3, leu2, his3) from the *Kluyveromyces marxianus* DMKU3-1042 strain (also referred to as "RAK3596"), and at the same time, introducing the xylose isomerase (XI) gene was prepared in the manner described below. The XI gene used herein is the RsXI-C1-opt (hereinafter referred to as "RsXI") gene prepared via total synthesis of the following gene with the adjustment of frequency of codon usage to that in yeast: the XI gene from a symbiotic protist in the gut of *Reticulitermes speratus* disclosed in JP Patent Publication (Kokai) No. 2011-147445 A, which is known to show activity in *Saccharomyces cerevisiae*. In addition, PrimeSTAR Max DNA Polymerase (Takara Bio, Shiga, Japan) was used in accordance with the manufacturer's protocol for PCR amplification.

A 1.0-Kb upstream fragment of the xyl2 gene (XYL2U (1.0 kb)) and a 1.0-Kb upstream fragment of the xyl2 gene (XYL2D (1.0 kb)) were PCR-amplified using genome DNA of the *K. marxianus* DMKU3-1042 strain as a template and primers Bss-XYL2U-F (gtaaaacgacggccagtgagcgcgccctgcaggatcgatctcacctgctaaaaccaaaaacac (SEQ ID NO: 37)) and TDH3-XYL2U-R (aactgaaaaagcgtgtttttattcggttgataatttgt-atttttgttat (SEQ ID NO: 38)) and primers XYL2D-F (acatgtttcaaaactgtgattgaacgttatttatg (SEQ ID NO: 39)) and Bss-XYL2D-R ((atgaccatgattacgccaagcgcgccctgcaggagggataggttccgctcctg (SEQ ID NO: 40)), respectively.

Next, an ScTDH3 promoter (0.7 Kb), an ScPGK1 terminator (0.25 Kb), and an ScLEU2 marker (2.2 Kb) were PCR-amplified using genome DNA of the *S. cerevisiae* S288C strain as a template and primers TDH3-F (gaataaaaaacacgcttttcagttcgagtttatcattatc (SEQ ID NO: 41)) and TDH3-R (tttggtttgtttgtttatgtgtgtttattcgaaactaagttc (SEQ ID NO: 42)), primers PGK1-F (tcgagattgaattgaattgaaatcga-tagatc (SEQ ID NO: 43)) and PGK1-R (taaacttaaaatacgct-gaacccgaac (SEQ ID NO: 44)), and primers PGK1t-LEU2-F (tcgggttcagcgtattttaagtttatcgaggagaacttctagtatatccac (SEQ ID NO: 45)) and XYL2D-LEU2-R (gttcaatcacagttttgaaacat-gttcgactacgtcgtaaggccgtttctg (SEQ ID NO: 46)), respectively.

The RsXI-C1 (1.3 kb) gene fragment was PCR-amplified using a vector comprising the RsXI gene subjected to total synthesis as a template and primers TDH3-RsXI-F (aacaca-cataaacaaacaaaccaaaatgtctcaaattttaaggatatccc (SEQ ID NO: 47)) and PGK1-RsXI-R (cgatttcaattcaattcaatctcgattatt-gaaacaaaatttggttaataatac (SEQ ID NO: 48)).

Figure 5:
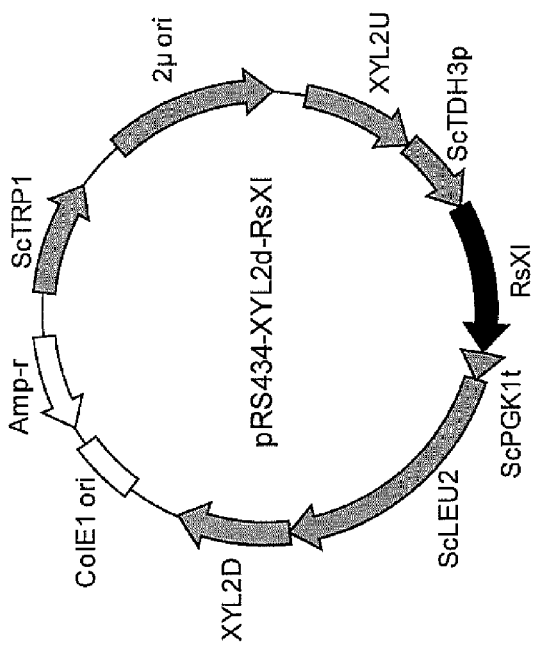
FIG. 5 shows a construct of pRS434XYL2d-RsXI.

Each of the PCR-amplified gene fragments was subjected to agarose gel electrophoresis. Bands with desired sizes were excised so as to be purified. The XYL2U, XYL2D, and ScTDH3 promoters, the ScPGK1 terminator, the ScLEU2 marker, and the RsXI gene fragment purified above were mixed, followed by fusion PCR using primers Bss-XYL2U-F and Bss-XYL2D-R. Thus, a DNA fragment comprising the individual genes ligated in series was synthesized. Then, the obtained DNA fragment was digested with the BssHII restriction enzyme and ligated to the BssHII site of a pRS434GAP vector (Genbank:AB304854). Thus, pRS434XYL2d-RsXI was prepared (FIG. 5).

The XYL2U-TDH3p-RsXI-PGK1t-ScLEU2-XYL2D region was PCR-amplified using pRS434XYL2d-RsXI as a template and primers XYL2U-F (atcgatctcttcctgctaaaac-caaaaac (SEQ ID NO: 49)) and XYL2D-R (agggataggttc-cgctcctgttggg (SEQ ID NO: 50)). RAK6163 was transformed with the obtained DNA fragment. The transformant was applied to an SD-Leu agar medium (Yeast Nitrogen Basewo amino acids (YNB) (Difco) (6.7 g/L), complete supplement mixture (CSM)-Leu(Bio101) (0.77 g/L), glucose (20 g/L), and agar (20 g/L)). The grown colonies were streaked again on an SD-Leu agar medium to obtain a single colony. Colony direct PCR was performed to confirm that the introduced gene fragment had been correctly inserted at the xyl2 gene locus and the xyl2 gene had been deleted. The transformant was designated the KM103 strain (xyl1::ScURA3, xyl2::RsXI-ScLEU2, his3).

[Preparation of an xyl1/xyl2 Double Deletion Mutant by Multicopy Integration of the XI Gene (i.e., the ScTHD3 Promoter)]

It is known that linear DNA fragments are randomly integrated on the genome of the *K. marxianus* DMKU3-1042 strain (Nonklang, S. et al, 2008. High-temperature ethanol fermentation and transformation with linear DNA in the thermotolerant yeast *Kluyveromyces marxianus* DMKU3-1042. Appl Environ Microbiol 74:7514-21). In view of this, it was attempted to carry out multicopy integration of synthesized linear DNA prepared by ligating an HIS3d marker cassette and an XI expression cassette on the *K. marxianus* genome.

First, an HIS3d marker fragment was PCR-amplified using genome DNA of the *S. cerevisiae* S288C strain as a template and primers HIS3d-F (caagataaacgaaggcaaagat-gacagag (SEQ ID NO: 51)) and HIS3d-R-5GCG (cccccggggccccccgcgcgcctcgttcagaatgacacgtatagaatg (SEQ ID NO: 52)). After the completion of reaction, the reaction solution was subjected to agarose gel electrophoresis and a desired DNA fragment was excised and purified by a standard method.

Next, the ScTDH3p-RsXI-ScPGK1t fragment was PCR-amplified using pRS434XYL2d-RsXI (FIG. 5) as a template and primers 5GCG-TDH3p-700F (ggggggc-ccccggggggaataaaaaacacgcttttcagttcgagtttatcattatc (SEQ ID NO: 53)) and PGK1t-R (taaacttaaaatacgctgaacccgaacata-gaaatatcg (SEQ ID NO: 54)). After the completion of reaction, the reaction solution was subjected to agarose gel electrophoresis and a desired DNA fragment was excised and purified by a standard method.

Then, the HIS3d marker fragment and the ScTDH3p-RsXI-ScPGK1t fragment were mixed and the two fragments were ligated by fusion PCR using primers HIS3d-F and PGK1t-R. The obtained fragment was introduced into the KM103 strain. Colonies were grown on an SD-His (comprising CSM-His instead of CSM-Leu used for an SD-Leu medium) agar medium. A strain obtained by refining the colonies was designated the KM203 strain. Specifically, the KM203 strain is a transformed strain obtained by multicopy integration of an expression cassette for expression of the XI gene with an ScTHD3 promoter.

[Preparation of an xyl1/xyl2 Double Deletion Mutant by Multicopy Integration of the XI Gene (Using KmPIR1 and KmCTR1 Promoters)]

A cassette for expression of the XI gene with a KmPIR1 promoter and a cassette for expression of the XI gene with a KmCTR1 promoter were prepared in the manner described below.

First, the HIS3d marker fragment was PCR-amplified using genome DNA of the *S. cerevisiae* S288C strain as a template and primers Bss-HIS3d-F (acgttgtaaaacgacggcca-gtgagcgcgccctgcagggaaggcaaagatgacagagcagaaagccc (SEQ ID NO: 55)) and HIS3d-R (gcgcgcctcgttcagaatgacacgtata-gaatg (SEQ ID NO: 56)).

Next, the KmPIR1 promoter fragment (2.92 kb) and the KmCTR1 promoter fragment (0.52 kb) were PCR-amplified using genome DNA of the *K. marxianus* DMKU3-1042 strain as a template and primers HIS3-KmPIR1-2921F (acgtgtcattctgaacgaggcgcgctgtataaattgaaatgtttggatt-gaaaagggaagc (SEQ ID NO: 57)) and KmPIR1-1R (tg-tataaatcggggtatgtgtgttggtaaaaacg (SEQ ID NO: 58)) and primers HIS3-KmCTR1-521F (acgtgtcattctgaacgag-gcgcgctcttggacaaaaaacgcatattgcgaggtttataac (SEQ ID NO: 59)) and KmCTR1-1R (cttgattgttcaattgtcaattgtcaatgggcttct-tgtcgtc (SEQ ID NO: 60)), respectively.

Then, the KmPIR1-RsXI-ScPGK1t fragment was PCR-amplified using pRS434XYL2d-RsXI (FIG. 5) as a template and primers KmPIR1-RsXI-F (acacacacataccccgatttatacaat-gtctcaaattttaaggatatcccagttattaaatatg (SEQ ID NO: 61)) and Bss-ScPGK1t-R (atgaccatgattacgccaagcgcgccctgcagg-taaacttaaaatacgctgaacccgaacatag (SEQ ID NO: 62)).

Figure 6:
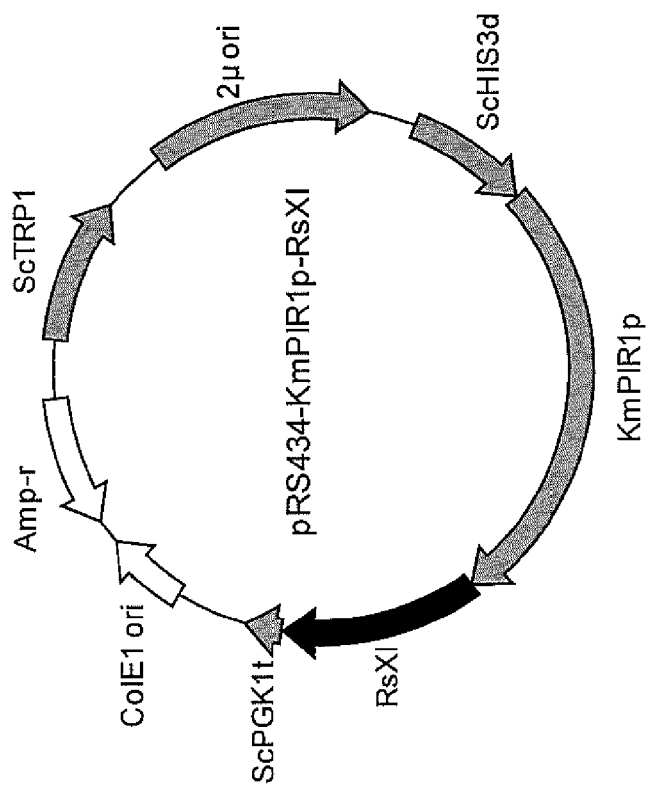
FIG. 6 shows a construct of pRS434KmPIR1p-RsXI.

Each of the DNA fragments PCR-amplified above was subjected to agarose gel electrophoresis and the desired DNA fragment was purified by a standard method. The obtained HIS3d marker fragment, KmPIR1 promoter fragment, and KmPIR1-RsXI-ScPGK1t fragment were mixed and the three fragments were ligated by fusion PCR using primers Bss-HIS3d-F and Bss-ScPGK1t-R. The obtained fragment was digested with restriction enzyme BssHII. The digested fragment was ligated to the BssHII site of a pRS434GAP vector so that pRS434KmPIR1p-RsXI was prepared (FIG. 6).

Figure 7:
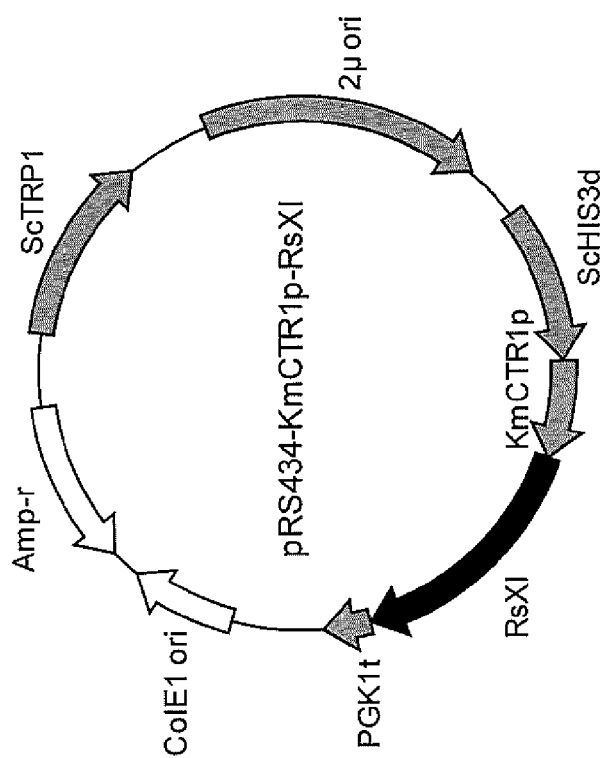
FIG. 7 shows a construct of pRS434KmCTR1p-RsXI.

Similarly, the KmCTR1-RsXI-ScPGK1t fragment was PCR-amplified using pRS434XYL2d-RsXI (FIG. 5) as a template and primers KmCTR1-RsXI-F (gacaattgacaatt-gaacaatcaagatgtctcaaattttaaggatatcccagttattaaatatg (SEQ ID NO: 63)) and Bss-ScPGK1t-R. The three fragments, i.e., the thus obtained fragment and the above fragments, were ligated by fusion PCR in the manner described above. The obtained fragment was ligated to the BssHII site of a pRS434GAP vector so that pRS434KmCTR1p-RsXI was prepared (FIG. 7)

Then, PCR was performed using pRS434KmPIR1p-RsXI (FIG. 6) and pRS434KmCTR1p-RsXI (FIG. 7) as templates and primers HIS3d-F and PGK1t-R. Accordingly, the ScHIS3-KmPIR1p-RsXI-ScPGK1t fragment and the ScHIS3-KmCTR1p-RsXI-ScPGK1t fragment were amplified. The obtained amplification fragments were separately introduced into the KM103 strain. Colonies were grown on an SD-His agar medium. The strains obtained by refining the colonies were designated the KM303 strain and the KM306 strain. Specifically, the KM303 strain and the KM306 strain are transformed strains into which an expression cassette for expression of the XI gene has been introduced by multicopy integration using the KmPIR1 promoter and the KmCTR1 promoter, respectively.

[Proliferation of the xyl1/xyl2 Double Deletion Mutant Transfected with the XI Gene in an Xylose Medium]

Figure 8:
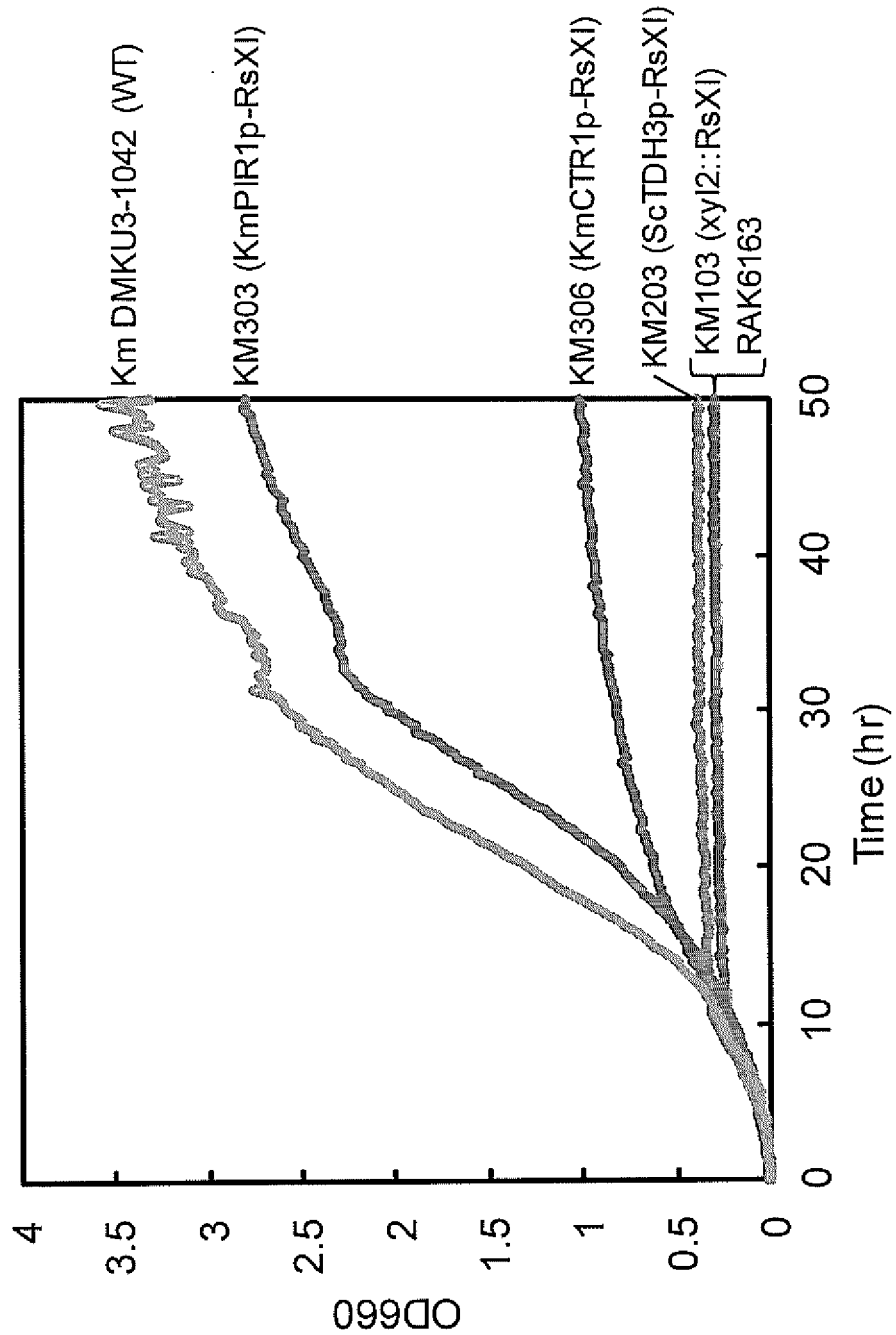
FIG. 8 is a characteristic chart showing proliferation test results for the DMKU3-1042, RAK6163, KM103, KM203, KM303, and KM306 strains.

The *K. marxianus* DMKU3-1042, RAK6163, KM103, KM203, KM303, and KM306 strains were separately inoculated to an SX medium (YNB: 6.7 g/L; CSM: 0.77 g/L; xylose: 20 g/L) with a carbon source (xylose) prepared in an L-shaped test tube (5 ml), followed by proliferation test. Proliferation test was carried out using a biophotorecorder TVS062CA (ADVANTEC, Tokyo, Japan) at 30 degrees C. and 70 rpm. FIG. 8 shows the proliferation test results.

As is understood from FIG. 8, the RAK6163, KM103, and KM203 strains were found to have slightly proliferated for up to about 10 hours by assimilating a small amount of glucose in the medium; however, the strains were unable to proliferate after 10 hours, indicating that they cannot proliferate using xylose as a carbon source. The results suggest that the xyl1 deletion strain (RAK6163) cannot proliferate using xylose as a carbon source, and that the RsXI genes to be expressed by the ScTDH3 promoter introduced onto the chromosome via single-copy integration or multicopy integration (i.e., KM103 and KM203) do not show XI activity sufficient for proliferation using xylose as a carbon source.

Meanwhile, as is understood from FIG. 8, the KM303 and KM306 strains were able to proliferate using xylose as a carbon source. The results indicate that each of RsXI to be expressed by the KmPIR1 promoter introduced onto the chromosome via multicopy integration and RsXI to be expressed by the KmCTR1 promoter introduced onto the chromosome via multicopy integration can express XI activity sufficient to proliferate using xylose as a carbon source.

Figure 9:
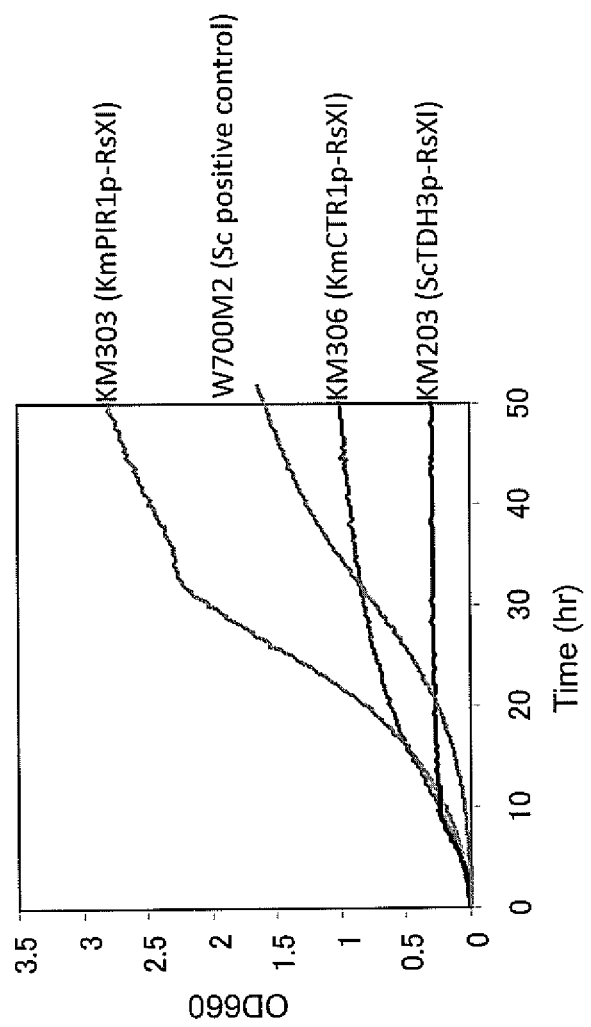
FIG. 9 is a characteristic chart showing proliferation test results for the KM203, KM303, KM306, and W700M2 strains.

In addition, FIG. 9 is a graph showing proliferation test results for the W700M2 strain compared with the proliferation test results for the KM203, KM303, and KM306 strains. Here, the W700M2 strain is a strain produced by improving the expression of the PPP gene and the XKS1 gene in the generally available *S. cerevisiae* W303-1B strain and integrating ScHOR7p-RsXI into a strain from which the GRE3 gene has been deleted. ScHOR7p-RsXI is a promoter for the *S. cerevisiae* HOR7 gene and known as a high expression promoter. The W700M2 strain is a gene recombinant having the above configuration, and thus it can proliferate using xylose as a carbon source. That is, the W700M2 strain can be used as a positive control in this experiment. As shown in FIG. 9, the KM303 and KM306 strains were found capable of proliferating using xylose as a carbon source, as well as the positive control, i.e., the W700M2 strain.

The above results revealed that the *K. marxianus* PIR1 promoter and the *K. Marxianus* CTR1 promoter show excellent promoter activity when used as a promoter for introducing a foreign gene into thermotolerant yeast and have ability to cause expression of the foreign gene to a sufficient extent.

[Reference Experiment]

*Kluyveromyces marxianus*, which is thermotolerant yeast, was analyzed by next-generation sequence transcription analysis in terms of gene expression upon xylose assimilation and glucose assimilation.

First, *Kluyveromyces marxianus* DMKU3-1042 was cultured separately in each of a YPD (2% glucose) medium and a YPX (2% xylose) medium for 18 hours. After culture, RNA was extracted and next-generation sequence transcription analysis was carried out via mRNA sequencing by a single-end method using Illumina GAII. The obtained data were assembled into a prepared draft genome sequence. Mapped regions were extracted and the number of reads per 100-bp region was calculated so that a transcript amount of the region was obtained.

In this experiment, more than 2000 genes expressed in either a YPD medium or a YPX medium were listed in the order of the transcript amount. Here, among predicted *Kluyveromyces marxianus* ORFs, an ORF that was not found among ORFs for *S. Cerevisiae* was named with a combination of four alphabetical letters and at least one numeric character. For example, when a specific ORF is not found among *S. Cerevisiae* ORFs as a result of mRNA sequencing, the specific ORF is named with a combination of four alphabetical letters defined by single letter notation for four amino acids from an ATG initiation codon and at least one numeric character indicating the nucleotide length of the ORF. For example, it can be named "MIFP960" or "MFRK1161." According to this nomenclature, among predicted *Kluyveromyces marxianus* ORFs, ORFs that do not correspond to *S. Cerevisiae* ORFs can be designated without repeating the use of the same names.

The *K. Marxianus* PIR1 gene and the *K. Marxianus* CTR1 gene examined in the above Examples were ranked after the 10th position in terms of the transcript amount for each medium. That is, promoters of the *K. Marxianus* PIR1 gene and the *K. Marxianus* CTR1 gene cannot be expected to function as high expression promoters based on the results of the Reference Experiment. Meanwhile, the TEF1 gene, the HSP26 gene, and the PCK1 gene examined in Example 1 for comparison were found to be expressed to a greater extent than the *K. Marxianus* PIR1 gene and the *K. Marxianus* CTR1 gene upon xylose or glucose assimilation. Accordingly, promoters of these TEF1, HSP26, and PCK1 genes can be regarded as more promising high expression promoter candidates than promoters of the *K. Marxianus* PIR1 gene and the *K. Marxianus* CTR1 gene.

Further, *Kluyveromyces marxianus* was evaluated in terms of gene expression upon xylose assimilation and glucose assimilation using a microarray. For microarray analysis, the NimbleGenmicroarray contract service provided by Roche Diagnostics was used. As an RNA sample, yeast was cultured in 2.5 ml of a YPD medium or YPX (containing 2% xylose instead of glucose used for YPD) medium for 24 hours and then prepared using a QIAGEN RNAeasy Mini Kit (Qiagen).

As a result of microarray analysis, it was revealed that the *K. Marxianus* PIR1 gene and the *K. Marxianus* CTR1 are not highly expressed in each medium. In particular, the *K. Marxianus* PIR1 gene was not ranked even within the top 100 genes. Based on these results, it was impossible for promoters of the *K. Marxianus* PIR1 gene and the *K. Marxianus* CTR1 gene to be expected to function as promoters that can be highly expressed in thermotolerant yeast.

The invention claimed is:

1. An isolated nucleic acid comprising a promoter sequence, wherein said promoter sequence consists of between 1000-2873 contiguous nucleotides of SEQ ID NO: 1, wherein said promoter sequence contains at least nucleotides 1874-2873 of SEQ ID NO: 1, and wherein said nucleic acid further comprises a nucleotide sequence heterologous to said promoter sequence.

2. The nucleic acid of claim 1, wherein said promoter sequence consists of between 2000-2873 contiguous nucleotides of SEQ ID NO: 1, and wherein said promoter sequence contains at least nucleotides 874-2873 of SEQ ID NO: 1.

3. An expression vector comprising a promoter sequence, wherein said promoter sequence consists of between 1000-2873 contiguous nucleotides of SEQ ID NO: 1, wherein said promoter sequence contains at least nucleotides 1874-2873 of SEQ ID NO: 1, and wherein in said expression vector, a coding sequence is operably linked to said promoter sequence.

4. The expression vector of claim 3, wherein said coding sequence is heterologous to said promoter sequence.

5. A transformant, wherein said transformant is a host cell transformed with the nucleic acid of claim 1.

6. The transformant of claim 5, wherein in said nucleic acid, said promoter sequence is operably linked to a heterologous coding sequence.

7. The transformant of claim 5, wherein the host cell is a thermotolerant yeast cell.

8. The transformant of claim 5, wherein said transformant is capable of causing saccharification of a cellulose-based biomass and ethanol fermentation.

9. The nucleic acid of claim 1, wherein in said nucleic acid, a coding sequence is operably linked to said promoter sequence.

10. An isolated nucleic acid comprising a promoter sequence, wherein said promoter sequence consists of a nucleotide sequence having at least 95% sequence identity to the following sequence: a sequence consisting of between 1000-2873 contiguous nucleotides of SEQ ID NO: 1, and containing at least nucleotides 1874-2873 of SEQ ID NO: 1, and wherein said nucleic acid further comprises a nucleotide sequence heterologous to said promoter sequence.

11. The nucleic acid of claim 10, wherein said promoter sequence consists of a nucleotide sequence having at least 95% sequence identity to the following sequence: a sequence consisting of between 2000-2873 contiguous nucleotides of SEQ ID NO: 1, and containing at least nucleotides 874-2873 of SEQ ID NO: 1.

12. The nucleic acid of claim 10, wherein in said nucleic acid, a heterologous coding sequence is operably linked to said promoter sequence.

13. The nucleic acid of claim 11, wherein in said nucleic acid, a heterologous coding sequence is operably linked to said promoter sequence.

* * * * *

SEQUENCE LISTING

```
<160> NUMBER OF SEQ ID NOS: 63

<210> SEQ ID NO 1
<211> LENGTH: 2873
<212> TYPE: DNA
<213> ORGANISM: Kluyveromyces marxianus

<400> SEQUENCE: 1
ggaaagagtc gatgtgattc gatgcttatt tcttgatgtt ctttgtgagt aacaaaagat      60
atgatataca actattagga aacatcaatc aagagatcca aaaaagtctg aaacctgtta     120
ctattttata cttttttggat ctcaagcgtc aatgaatctt ttgtgtgtca attgtgctgg    180
gaacaatgtc gaaatctaaa ctgtgatcca acatgcacaa aattgaagca agcatcattt     240
tttgatccat agacagaccc gtatatgcat actccagtgg tttcctggta cctgtactct     300
cttgcctgag aaactaaaac caggaatcaa agcttgaaag ttaccagaca aattgccgaa     360
ttcgatatat tgatcccagc aaaaaaatta gaaatagtag cattagcctc tctttgatca     420
atgaatactg aggaaaaggt aatcatcgga caatagagct cgacagtact caactcaaga    480
agagtgactg agggaaaata aaccacaacc agccactcgt tcccctttgg taccttcgt     540 cctacgtaga tctgtatgtg ctttgtgtgt atttttttt ttccgttaca gaatattcgc     600
accatgaaat ttcaagctgg ttaaaaaaat taatgtcaat ttgaaaaccc agcgatcttg     660
gaaaaacatg gaagaacaga aatagaaata caaatggaaa aagcttccta ctacgttctc    720
agtgggagaa ataaaaatag caatccattt tttttgattg agccagcagc aggtagacag    780
gcacagcagc aacggcagcg gctggttcaa atcgatcctg attcagcaat gagtaagtag    840
gacatgctgg gatcacacgg cttgattgat ccagcaaagc ccgatccggt tctaatgtta    900
gattcaacgg ccataccggc taaagacgtg ctattgctgg gccgccattc tccatgagct     960
acataagccg tatatagatg aaacaaattg agtgtgtgcg tgtgtgtgtt ttattagcct    1020 tcatttttt ttcattttaa attatggtca cgtgacacac ttcactttc atttttagtt     1080 tttcgttttt tcgcttttcc tccctttcc ttccgaagtt gaaaattgca aatgaagaga   1140
acagaaaagc gcattctcat tcggcccgga agagaatgtc cccgtctccg ccgaaatttt    1200
cttatttcgg tgttcccgaa aaagccatta atattcttaa acaggtaatt aaagcaccga    1260
aaacgtccga tacagaccta aaagggtaaa agtaaaatat tctccagtac gactggtgaa    1320
tttcccgaga gggaaataca tttcattact tgaatagact aactaactaa ctaactaact    1380
agtcaggcac cactgtcaac acgaagtcca accttactcc gtcagaaccc tctaccctg    1440
```

| | |
|---|---|
| accccttgtaa tagcagaatc agaagcagaa gcagcagcta ctacagctac tacagctacc | 1500 |
| cgaaccctat cccaacccat ccttgtaaat accctgttag gatataccctc gtgtgaacag | 1560 |
| cgctgcacca cccttgccta acgaccccaa atccggtcta aaaaatagtg taccctgccg | 1620 |
| tatataccctg aaagttgatc tatgccggga cggcttacgc ctcttaaatc ccagatctac | 1680 |
| atggatttag tgaaagaaaa aacgagaatt gaacagacta ccactcatac ccacgcacac | 1740 |
| acatacaccc ttgagaaaaa ttacaaaaaa aaccctcca tttcccaatt tccccttctt | 1800 |
| cttttttgca atgcggaaga aaacagaaaa cataccagtc agtccatcgt caatccccctc | 1860 |
| gtttctcgct taaacccatc attattatta ttcattattc cacttctcgt tattacctca | 1920 |
| gatatacacc gtttgtacgt gagaatgaga gcttagcccc aatcttagta aatcaagagt | 1980 |
| aagtaaaaaa acactaaaaa aaaaaattac agtgccatta gtactagtag tactagtgat | 2040 |
| tagtgggtgt atgcggaata gtaagtacga gcaagagccc tacctactaa tgccgctacc | 2100 |
| actattatgc tattccgcct tgggttgcca aggccctggg gccggtgga tttctacttc | 2160 |
| ctacatcact cacacgcccg cagcaacag ttcactaccc gaataagaat gtcgatgtca | 2220 |
| taggtaaata ccatagcgac aacctactgc cattgcaaca agcaaatatc accctctaat | 2280 |
| ggttgtggct tttgcaagaa ttcggatcca aaccgaattg atttcgattt gatttgctca | 2340 |
| tctaactatt ccttaagaag taaagaaatg attggaatca ggaaccgaag gcgttcccca | 2400 |
| ttaacaacct cgcacaaaga tgtaaaaaaa ttctttgaat gatcctactt tattttttt | 2460 |
| ttttgatttg tgcttctgct tcctcttatt ctgcggcctt tttctcgaga ttttctcatt | 2520 |
| ttgttcctat ttggatccca cttagttctc aattcggaaa agctattggc aaagaacagg | 2580 |
| tgagagggga aggttttggc aggaaagtta ttttagaac ggtttatcca caccatacca | 2640 |
| tagtatctac cattagtatt gtttgctcga tgccccaaag caagaaagg attagagatg | 2700 |
| ttgaaaggtt ttcgaaattg tatataaaga gaggatggat gagatgttaa tttggaatct | 2760 |
| gtttgtcttg tatgtatcta tatctgttgt agattatatc ttgaataaca ctcaaaacag | 2820 |
| taatcaacag atccaatcgt ttttaccaac acacacatac cccgatttat aca | 2873 |

<210> SEQ ID NO 2
<211> LENGTH: 840
<212> TYPE: DNA
<213> ORGANISM: Kluyveromyces marxianus

<400> SEQUENCE: 2

| | |
|---|---|
| taggatcagg agacaatcga tattacacca aatacgtaac agcacaggtc cctccatcaa | 60 |
| caatgctgca tctacgaatc caaattcaaa cactcaaaga aaaagatcat tagctgtaag | 120 |
| tgctaaaaga ataccctccc aggcgggccc atctgcatct gccatcattt ctacgaacaa | 180 |
| caataccaag agtaacaccg aaaataatca aaaaaatggc atatcaatat cgggccctgg | 240 |
| aaatagattt cgcaccccgc gaccaagaca acgaacatat cagagtaaag acttgtctag | 300 |
| cagaccacct ttcagatagt cttggacaaa aaacgcatat tgcgaggttt ataacagtac | 360 |
| ataaaagcta gaaaaccgtt gtaacactga aacaacaaa tcctaataat actctcacat | 420 |
| tgttactttg agcaattact ttgatgataa ataacaggtg ctgaaaagtg cctgtacatc | 480 |
| cccagactaa tattcaaata gctgtgctct cttttatt tttttctct ctttctctct | 540 |
| tcgttttctc tgttgtaatg tactcacgct cttaaagagc atattgagca aataaagtat | 600 |
| tcgtatgaga aaaaaacgag ttgatttaaa ggcaagtgaa gcagcacgag gaagaggtgc | 660 |
| gttggaatat cttcccgga ctttatataa agagatgtca gtctagcggt atcgagtgtt | 720 | tatttcggtg tcttggcctt ttctaaggta gtgctgtgat tgaatgcaac acaatactgt    780 cctgaggtaa acgagaagac gacaagaagc ccattgacaa ttgacaattg aacaatcaag    840

<210> SEQ ID NO 3
<211> LENGTH: 25
<212> TYPE: DNA
<213> ORGANISM: Artificial
<220> FEATURE:
<223> OTHER INFORMATION: Synthetic DNA

<400> SEQUENCE: 3
taggatcagg agacaatcga tatta    25

<210> SEQ ID NO 4
<211> LENGTH: 55
<212> TYPE: DNA
<213> ORGANISM: Artificial
<220> FEATURE:
<223> OTHER INFORMATION: Synthetic DNA

<400> SEQUENCE: 4
caaagcgaca gccaagatca aggtcttcat cttgattgtt caattgtcaa ttgtc    55

<210> SEQ ID NO 5
<211> LENGTH: 20
<212> TYPE: DNA
<213> ORGANISM: Artificial
<220> FEATURE:
<223> OTHER INFORMATION: Synthetic DNA

<400> SEQUENCE: 5
atgaagacct tgatcttggc    20

<210> SEQ ID NO 6
<211> LENGTH: 23
<212> TYPE: DNA
<213> ORGANISM: Artificial
<220> FEATURE:
<223> OTHER INFORMATION: Synthetic DNA

<400> SEQUENCE: 6
cagtctgtga aacatctttc tac    23

<210> SEQ ID NO 7
<211> LENGTH: 25
<212> TYPE: DNA
<213> ORGANISM: Artificial
<220> FEATURE:
<223> OTHER INFORMATION: Synthetic DNA

<400> SEQUENCE: 7
ggaaagagtc gatgtgattc gatgc    25

<210> SEQ ID NO 8
<211> LENGTH: 40
<212> TYPE: DNA
<213> ORGANISM: Artificial
<220> FEATURE:
<223> OTHER INFORMATION: Synthetic DNA

<400> SEQUENCE: 8
tgtgtgtgtg tgtgtgtgtg tgtataaatc ggggtatgtg    40

<210> SEQ ID NO 9

```
<211> LENGTH: 40
<212> TYPE: DNA
<213> ORGANISM: Artificial
<220> FEATURE:
<223> OTHER INFORMATION: Synthetic DNA

<400> SEQUENCE: 9
cacacacaca cacacacaca atgaagacct tgatcttggc                    40

<210> SEQ ID NO 10
<211> LENGTH: 25
<212> TYPE: DNA
<213> ORGANISM: Artificial
<220> FEATURE:
<223> OTHER INFORMATION: Synthetic DNA

<400> SEQUENCE: 10
gagaagggca acggttcatc atctc                                    25

<210> SEQ ID NO 11
<211> LENGTH: 35
<212> TYPE: DNA
<213> ORGANISM: Artificial
<220> FEATURE:
<223> OTHER INFORMATION: Synthetic DNA

<400> SEQUENCE: 11
gggggggggg ggggctact tgcactcatc tggga                          35

<210> SEQ ID NO 12
<211> LENGTH: 45
<212> TYPE: DNA
<213> ORGANISM: Artificial
<220> FEATURE:
<223> OTHER INFORMATION: Synthetic DNA

<400> SEQUENCE: 12
cccccccccc cccccaagct ttcaattca tctttttttt ttttg               45

<210> SEQ ID NO 13
<211> LENGTH: 25
<212> TYPE: DNA
<213> ORGANISM: Artificial
<220> FEATURE:
<223> OTHER INFORMATION: Synthetic DNA

<400> SEQUENCE: 13
ggcggataaa atggtactat tacgt                                    25

<210> SEQ ID NO 14
<211> LENGTH: 55
<212> TYPE: DNA
<213> ORGANISM: Artificial
<220> FEATURE:
<223> OTHER INFORMATION: Synthetic DNA

<400> SEQUENCE: 14
caaagcgaca gccaagatca aggtcttcat ttttgatttg tgtttaagcg agtga   55

<210> SEQ ID NO 15
<211> LENGTH: 25
<212> TYPE: DNA
<213> ORGANISM: Artificial
<220> FEATURE:
<223> OTHER INFORMATION: Synthetic DNA

<400> SEQUENCE: 15
```
ctattgcttc gcttccctgc atcag                                              25

<210> SEQ ID NO 16
<211> LENGTH: 55
<212> TYPE: DNA
<213> ORGANISM: Artificial
<220> FEATURE:
<223> OTHER INFORMATION: Synthetic DNA

<400> SEQUENCE: 16
caaagcgaca gccaagatca aggtcttcat gtctgctaaa agttcaaaat taatt           55

<210> SEQ ID NO 17
<211> LENGTH: 25
<212> TYPE: DNA
<213> ORGANISM: Artificial
<220> FEATURE:
<223> OTHER INFORMATION: Synthetic DNA

<400> SEQUENCE: 17
ttgggctaga gcaaaaaacc ccaac                                              25

<210> SEQ ID NO 18
<211> LENGTH: 55
<212> TYPE: DNA
<213> ORGANISM: Artificial
<220> FEATURE:
<223> OTHER INFORMATION: Synthetic DNA

<400> SEQUENCE: 18
caaagcgaca gccaagatca aggtcttcat ctcgtaatcg cttttgttct tagtt           55

<210> SEQ ID NO 19
<211> LENGTH: 25
<212> TYPE: DNA
<213> ORGANISM: Artificial
<220> FEATURE:
<223> OTHER INFORMATION: Synthetic DNA

<400> SEQUENCE: 19
gtgttgtaac aagctgccat ataga                                              25

<210> SEQ ID NO 20
<211> LENGTH: 55
<212> TYPE: DNA
<213> ORGANISM: Artificial
<220> FEATURE:
<223> OTHER INFORMATION: Synthetic DNA

<400> SEQUENCE: 20
caaagcgaca gccaagatca aggtcttcat ctttaatgtt acttctcttg gagtt           55

<210> SEQ ID NO 21
<211> LENGTH: 25
<212> TYPE: DNA
<213> ORGANISM: Artificial
<220> FEATURE:
<223> OTHER INFORMATION: Synthetic DNA

<400> SEQUENCE: 21
atatcgtctt attccattaa taacc                                              25

<210> SEQ ID NO 22
<211> LENGTH: 55
<212> TYPE: DNA

<213> ORGANISM: Artificial
<220> FEATURE:
<223> OTHER INFORMATION: Synthetic DNA

<400> SEQUENCE: 22
caaagcgaca gccaagatca aggtcttcat ggtgacttat tattattaga aacaa    55

<210> SEQ ID NO 23
<211> LENGTH: 25
<212> TYPE: DNA
<213> ORGANISM: Artificial
<220> FEATURE:
<223> OTHER INFORMATION: Synthetic DNA

<400> SEQUENCE: 23
ttctagttgt tggttgttgt ttttg    25

<210> SEQ ID NO 24
<211> LENGTH: 55
<212> TYPE: DNA
<213> ORGANISM: Artificial
<220> FEATURE:
<223> OTHER INFORMATION: Synthetic DNA

<400> SEQUENCE: 24
caaagcgaca gccaagatca aggtcttcat cttttaaaat tatctgagtt gagtt    55

<210> SEQ ID NO 25
<211> LENGTH: 25
<212> TYPE: DNA
<213> ORGANISM: Artificial
<220> FEATURE:
<223> OTHER INFORMATION: Synthetic DNA

<400> SEQUENCE: 25
gtcacgtgtg tatccggcgg gtaaa    25

<210> SEQ ID NO 26
<211> LENGTH: 55
<212> TYPE: DNA
<213> ORGANISM: Artificial
<220> FEATURE:
<223> OTHER INFORMATION: Synthetic DNA

<400> SEQUENCE: 26
caaagcgaca gccaagatca aggtcttcat tgtgttgtgt atgattttgt tttta    55

<210> SEQ ID NO 27
<211> LENGTH: 20
<212> TYPE: DNA
<213> ORGANISM: Artificial
<220> FEATURE:
<223> OTHER INFORMATION: Synthetic DNA

<400> SEQUENCE: 27
gagtgcggag tcagatacaa    20

<210> SEQ ID NO 28
<211> LENGTH: 55
<212> TYPE: DNA
<213> ORGANISM: Artificial
<220> FEATURE:
<223> OTHER INFORMATION: Synthetic DNA

<400> SEQUENCE: 28
caaagcgaca gccaagatca aggtcttcat tgttgcgtga tattttctgt gcctg    55

```
<210> SEQ ID NO 29
<211> LENGTH: 22
<212> TYPE: DNA
<213> ORGANISM: Artificial
<220> FEATURE:
<223> OTHER INFORMATION: Synthetic DNA

<400> SEQUENCE: 29
gcaaagcccg atccggttct aa                                              22

<210> SEQ ID NO 30
<211> LENGTH: 22
<212> TYPE: DNA
<213> ORGANISM: Artificial
<220> FEATURE:
<223> OTHER INFORMATION: Synthetic DNA

<400> SEQUENCE: 30
caatcccctc gtttctcgct ta                                              22

<210> SEQ ID NO 31
<211> LENGTH: 22
<212> TYPE: DNA
<213> ORGANISM: Artificial
<220> FEATURE:
<223> OTHER INFORMATION: Synthetic DNA

<400> SEQUENCE: 31
ggaatcagga accgaaggcg tt                                              22

<210> SEQ ID NO 32
<211> LENGTH: 22
<212> TYPE: DNA
<213> ORGANISM: Artificial
<220> FEATURE:
<223> OTHER INFORMATION: Synthetic DNA

<400> SEQUENCE: 32
cggtttatcc acaccatacc at                                              22

<210> SEQ ID NO 33
<211> LENGTH: 23
<212> TYPE: DNA
<213> ORGANISM: Artificial
<220> FEATURE:
<223> OTHER INFORMATION: Synthetic DNA

<400> SEQUENCE: 33
gctagaaaac cgttgtaaca ctg                                             23

<210> SEQ ID NO 34
<211> LENGTH: 22
<212> TYPE: DNA
<213> ORGANISM: Artificial
<220> FEATURE:
<223> OTHER INFORMATION: Synthetic DNA

<400> SEQUENCE: 34
ctctcacatt gttactttga gc                                              22

<210> SEQ ID NO 35
<211> LENGTH: 20
<212> TYPE: DNA
<213> ORGANISM: Artificial
<220> FEATURE:
```

```
<223> OTHER INFORMATION: Synthetic DNA

<400> SEQUENCE: 35
ggtgctgaaa agtgcctgta                                              20

<210> SEQ ID NO 36
<211> LENGTH: 25
<212> TYPE: DNA
<213> ORGANISM: Artificial
<220> FEATURE:
<223> OTHER INFORMATION: Synthetic DNA

<400> SEQUENCE: 36
ctctctttct ctcttcgttt ttctt                                        25

<210> SEQ ID NO 37
<211> LENGTH: 64
<212> TYPE: DNA
<213> ORGANISM: Artificial
<220> FEATURE:
<223> OTHER INFORMATION: Synthetic DNA

<400> SEQUENCE: 37
gtaaaacgac ggccagtgag cgcgccctgc aggatcgatc tcttcctgct aaaaccaaaa  60
acac                                                               64

<210> SEQ ID NO 38
<211> LENGTH: 50
<212> TYPE: DNA
<213> ORGANISM: Artificial
<220> FEATURE:
<223> OTHER INFORMATION: Synthetic DNA

<400> SEQUENCE: 38
aactgaaaaa gcgtgttttt tattcggttg ataatttgta ttttgttat              50

<210> SEQ ID NO 39
<211> LENGTH: 35
<212> TYPE: DNA
<213> ORGANISM: Artificial
<220> FEATURE:
<223> OTHER INFORMATION: Synthetic DNA

<400> SEQUENCE: 39
acatgtttca aaactgtgat tgaacgttat ttatg                             35

<210> SEQ ID NO 40
<211> LENGTH: 53
<212> TYPE: DNA
<213> ORGANISM: Artificial
<220> FEATURE:
<223> OTHER INFORMATION: Synthetic DNA

<400> SEQUENCE: 40
atgaccatga ttacgccaag cgcgccctgc aggagggata ggttccgctc ctg         53

<210> SEQ ID NO 41
<211> LENGTH: 41
<212> TYPE: DNA
<213> ORGANISM: Artificial
<220> FEATURE:
<223> OTHER INFORMATION: Synthetic DNA

<400> SEQUENCE: 41
gaataaaaaa cacgcttttt cagttcgagt ttatcattat c                      41
```

<210> SEQ ID NO 42
<211> LENGTH: 42
<212> TYPE: DNA
<213> ORGANISM: Artificial
<220> FEATURE:
<223> OTHER INFORMATION: Synthetic DNA

<400> SEQUENCE: 42
tttggtttgt ttgtttatgt gtgtttattc gaaactaagt tc                           42

<210> SEQ ID NO 43
<211> LENGTH: 32
<212> TYPE: DNA
<213> ORGANISM: Artificial
<220> FEATURE:
<223> OTHER INFORMATION: Synthetic DNA

<400> SEQUENCE: 43
tcgagattga attgaattga aatcgataga tc                                     32

<210> SEQ ID NO 44
<211> LENGTH: 27
<212> TYPE: DNA
<213> ORGANISM: Artificial
<220> FEATURE:
<223> OTHER INFORMATION: Synthetic DNA

<400> SEQUENCE: 44
taaacttaaa atacgctgaa cccgaac                                           27

<210> SEQ ID NO 45
<211> LENGTH: 51
<212> TYPE: DNA
<213> ORGANISM: Artificial
<220> FEATURE:
<223> OTHER INFORMATION: Synthetic DNA

<400> SEQUENCE: 45
tcgggttcag cgtattttaa gtttatcgag gagaacttct agtatatcca c                51

<210> SEQ ID NO 46
<211> LENGTH: 51
<212> TYPE: DNA
<213> ORGANISM: Artificial
<220> FEATURE:
<223> OTHER INFORMATION: Synthetic DNA

<400> SEQUENCE: 46
gttcaatcac agttttgaaa catgttcgac tacgtcgtaa ggccgtttct g                51

<210> SEQ ID NO 47
<211> LENGTH: 51
<212> TYPE: DNA
<213> ORGANISM: Artificial
<220> FEATURE:
<223> OTHER INFORMATION: Synthetic DNA

<400> SEQUENCE: 47
aacacacata aacaaacaaa ccaaaatgtc tcaaattttt aaggatatcc c                51

<210> SEQ ID NO 48
<211> LENGTH: 54
<212> TYPE: DNA
<213> ORGANISM: Artificial
<220> FEATURE:

<223> OTHER INFORMATION: Synthetic DNA

<400> SEQUENCE: 48
cgatttcaat tcaattcaat ctcgattatt gaaacaaaat ttggttaata atac             54

<210> SEQ ID NO 49
<211> LENGTH: 29
<212> TYPE: DNA
<213> ORGANISM: Artificial
<220> FEATURE:
<223> OTHER INFORMATION: Synthetic DNA

<400> SEQUENCE: 49
atcgatctct tcctgctaaa accaaaaac                                         29

<210> SEQ ID NO 50
<211> LENGTH: 25
<212> TYPE: DNA
<213> ORGANISM: Artificial
<220> FEATURE:
<223> OTHER INFORMATION: Synthetic DNA

<400> SEQUENCE: 50
agggataggt tccgctcctg ttggg                                             25

<210> SEQ ID NO 51
<211> LENGTH: 29
<212> TYPE: DNA
<213> ORGANISM: Artificial
<220> FEATURE:
<223> OTHER INFORMATION: Synthetic DNA

<400> SEQUENCE: 51
caagataaac gaaggcaaag atgacagag                                         29

<210> SEQ ID NO 52
<211> LENGTH: 48
<212> TYPE: DNA
<213> ORGANISM: Artificial
<220> FEATURE:
<223> OTHER INFORMATION: Synthetic DNA

<400> SEQUENCE: 52
cccccggggg cccccgcgcg cctcgttcag aatgacacgt atagaatg                    48

<210> SEQ ID NO 53
<211> LENGTH: 56
<212> TYPE: DNA
<213> ORGANISM: Artificial
<220> FEATURE:
<223> OTHER INFORMATION: Synthetic DNA

<400> SEQUENCE: 53
gggggccccc gggggaata aaaaacacgc tttttcagtt cgagtttatc attatc            56

<210> SEQ ID NO 54
<211> LENGTH: 39
<212> TYPE: DNA
<213> ORGANISM: Artificial
<220> FEATURE:
<223> OTHER INFORMATION: Synthetic DNA

<400> SEQUENCE: 54
taaacttaaa atacgctgaa cccgaacata gaaatatcg                              39

<210> SEQ ID NO 55
<211> LENGTH: 67
<212> TYPE: DNA
<213> ORGANISM: Artificial
<220> FEATURE:
<223> OTHER INFORMATION: Synthetic DNA

<400> SEQUENCE: 55
acgttgtaaa acgacggcca gtgagcgcgc cctgcaggga aggcaaagat gacagagcag    60
aaagccc                                                              67

<210> SEQ ID NO 56
<211> LENGTH: 33
<212> TYPE: DNA
<213> ORGANISM: Artificial
<220> FEATURE:
<223> OTHER INFORMATION: Synthetic DNA

<400> SEQUENCE: 56
gcgcgcctcg ttcagaatga cacgtataga atg                                 33

<210> SEQ ID NO 57
<211> LENGTH: 61
<212> TYPE: DNA
<213> ORGANISM: Artificial
<220> FEATURE:
<223> OTHER INFORMATION: Synthetic DNA

<400> SEQUENCE: 57
acgtgtcatt ctgaacgagg cgcgctgtat aaattgaaat gtttggattg aaagggaag     60 c                                                                    61

<210> SEQ ID NO 58
<211> LENGTH: 36
<212> TYPE: DNA
<213> ORGANISM: Artificial
<220> FEATURE:
<223> OTHER INFORMATION: Synthetic DNA

<400> SEQUENCE: 58
tgtataaatc ggggtatgtg tgtgttggta aaaacg                              36

<210> SEQ ID NO 59
<211> LENGTH: 61
<212> TYPE: DNA
<213> ORGANISM: Artificial
<220> FEATURE:
<223> OTHER INFORMATION: Synthetic DNA

<400> SEQUENCE: 59
acgtgtcatt ctgaacgagg cgcgctcttg gacaaaaaac gcatattgcg aggtttataa    60
c                                                                    61

<210> SEQ ID NO 60
<211> LENGTH: 43
<212> TYPE: DNA
<213> ORGANISM: Artificial
<220> FEATURE:
<223> OTHER INFORMATION: Synthetic DNA

<400> SEQUENCE: 60
cttgattgtt caattgtcaa ttgtcaatgg gcttcttgtc gtc                      43

<210> SEQ ID NO 61

```
<211> LENGTH: 65
<212> TYPE: DNA
<213> ORGANISM: Artificial
<220> FEATURE:
<223> OTHER INFORMATION: Synthetic DNA

<400> SEQUENCE: 61
acacacacat accccgattt atacaatgtc tcaaattttt aaggatatcc cagttattaa      60
atatg                                                                 65

<210> SEQ ID NO 62
<211> LENGTH: 64
<212> TYPE: DNA
<213> ORGANISM: Artificial
<220> FEATURE:
<223> OTHER INFORMATION: Synthetic DNA

<400> SEQUENCE: 62
atgaccatga ttacgccaag cgcgccctgc aggtaaactt aaaatacgct gaacccgaac      60
atag                                                                  64

<210> SEQ ID NO 63
<211> LENGTH: 65
<212> TYPE: DNA
<213> ORGANISM: Artificial
<220> FEATURE:
<223> OTHER INFORMATION: Synthetic DNA

<400> SEQUENCE: 63
gacaattgac aattgaacaa tcaagatgtc tcaaattttt aaggatatcc cagttattaa      60
atatg                                                                 65
```